(12) United States Patent
Kuwabara

(10) Patent No.: US 9,510,794 B2
(45) Date of Patent: Dec. 6, 2016

(54) RADIATION IMAGE CAPTURE DEVICE, CONTROL METHOD FOR ERASING LIGHT SOURCE, AND COMPUTER-READABLE STORAGE MEDIUM

(71) Applicant: FUJIFILM CORPORATION, Tokyo (JP)

(72) Inventor: Takao Kuwabara, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 274 days.

(21) Appl. No.: 14/505,637

(22) Filed: Oct. 3, 2014

(65) Prior Publication Data

US 2015/0097127 A1 Apr. 9, 2015

(30) Foreign Application Priority Data

Oct. 4, 2013 (JP) ................................ 2013-209451

(51) Int. Cl.

| | |
|---|---|
| *G01N 23/04* | (2006.01) |
| *A61B 6/04* | (2006.01) |
| *A61B 6/00* | (2006.01) |
| *G01T 1/24* | (2006.01) |
| *A61B 6/02* | (2006.01) |

(52) U.S. Cl.
CPC ................ *A61B 6/04* (2013.01); *A61B 6/025* (2013.01); *A61B 6/487* (2013.01); *A61B 6/502* (2013.01); *A61B 6/54* (2013.01); *G01T 1/24* (2013.01); *G01T 1/246* (2013.01); *A61B 6/461* (2013.01)

(58) Field of Classification Search
CPC ........... G01T 1/246; G01T 1/24; A61B 6/0256
See application file for complete search history.

(56) References Cited

U.S. PATENT DOCUMENTS

| 8,729,484 B2 * | 5/2014 | Nishino ................ G01T 1/2018 |
| | | 250/370.09 |
| 2007/0036265 A1 * | 2/2007 | Jing ........................ A61B 6/025 |
| | | 378/37 |

FOREIGN PATENT DOCUMENTS

| JP | 2002-296713 A | 10/2002 |
| JP | 2009-011526 A | 1/2009 |

* cited by examiner

*Primary Examiner* — David J Makiya
*Assistant Examiner* — Kenneth J Malkowski
(74) *Attorney, Agent, or Firm* — Birch, Stewart, Kolasch & Birch, LLP

(57) ABSTRACT

A radiation image capture device is provided that are capable of obtaining radiation images with better image quality than hitherto in both an imaging mode in which a radiation irradiation duration is comparatively short and radiation images are successively captured, and in an imaging mode in which the radiation irradiation duration is comparatively long. An erasing light source is deactivated throughout an imaging period in a first imaging mode in which a radiation detector generates image data of a radiation image based on radiation irradiated from a radiation source over a first irradiation duration. The erasing light source is activated over an imaging period in a second imaging mode in which the radiation detector generates image data of plural radiation images based on successively irradiated radiation from the radiation source over a second irradiation duration shorter than the first irradiation duration.

19 Claims, 19 Drawing Sheets

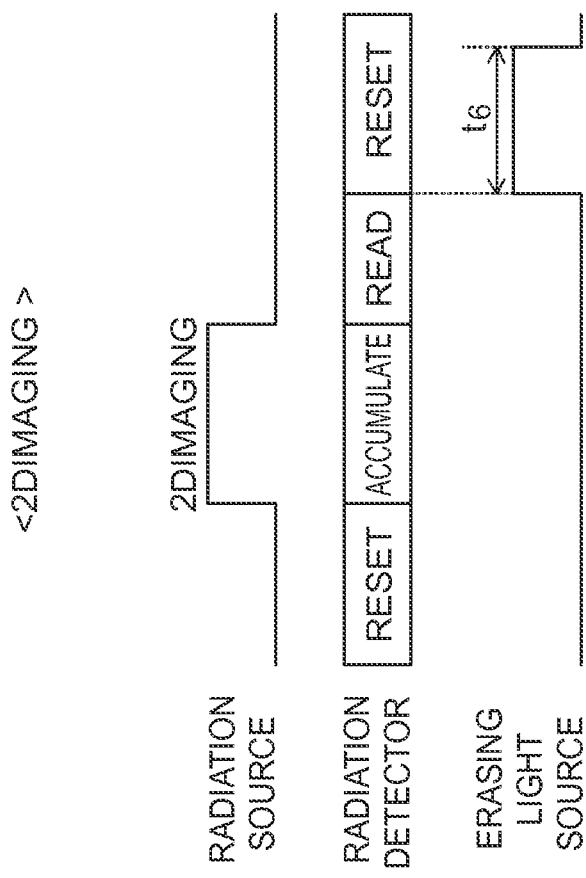

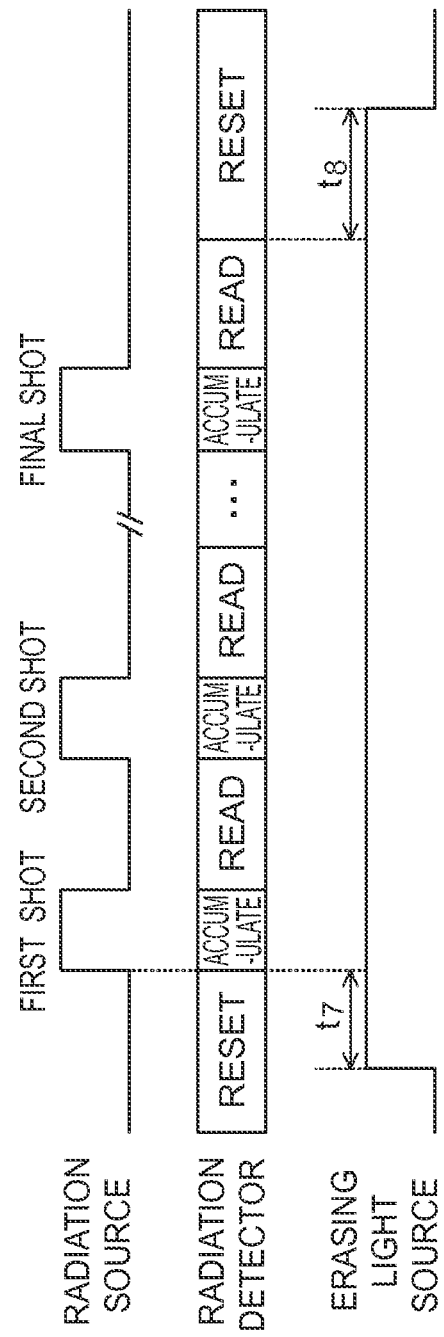

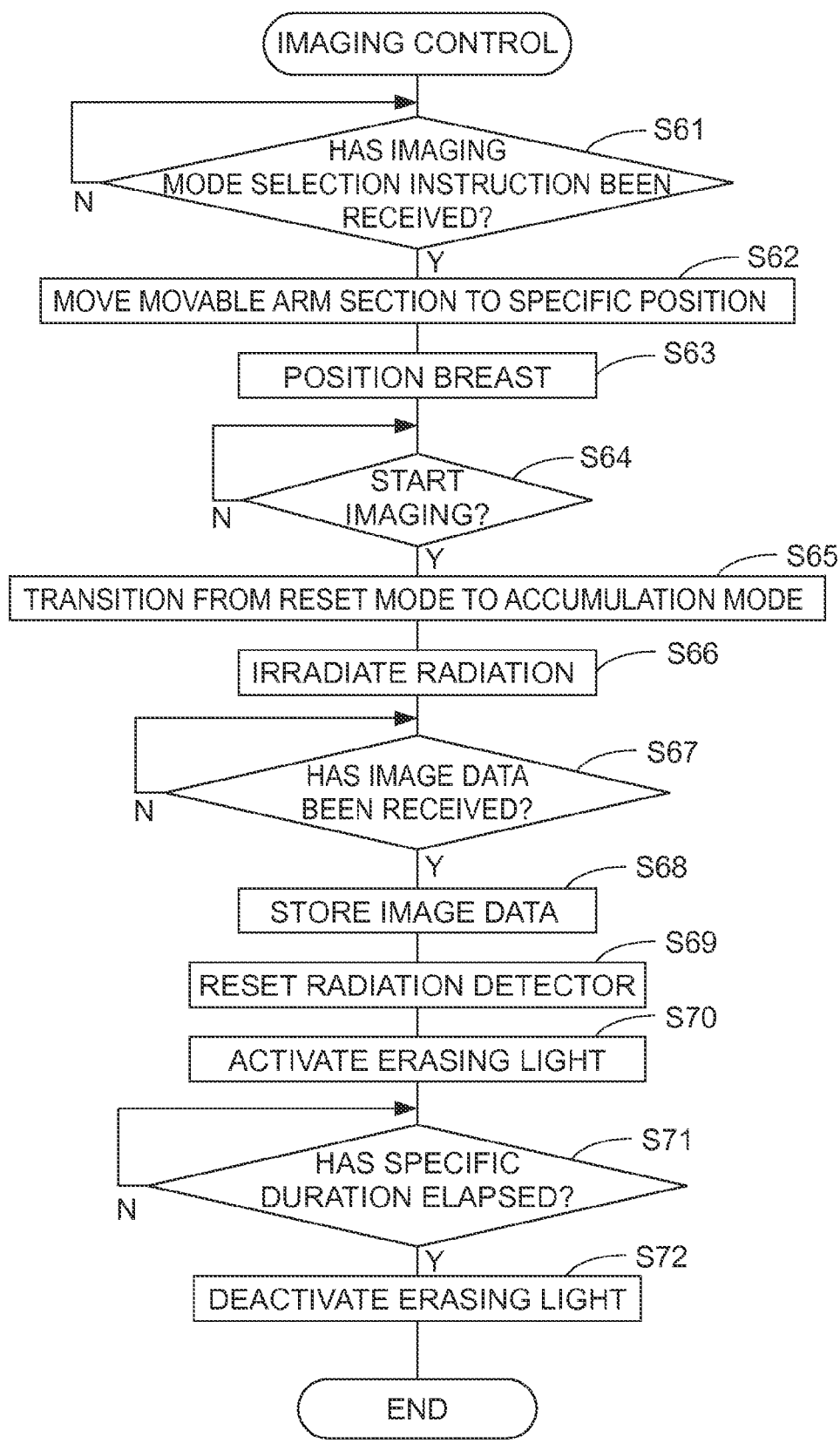

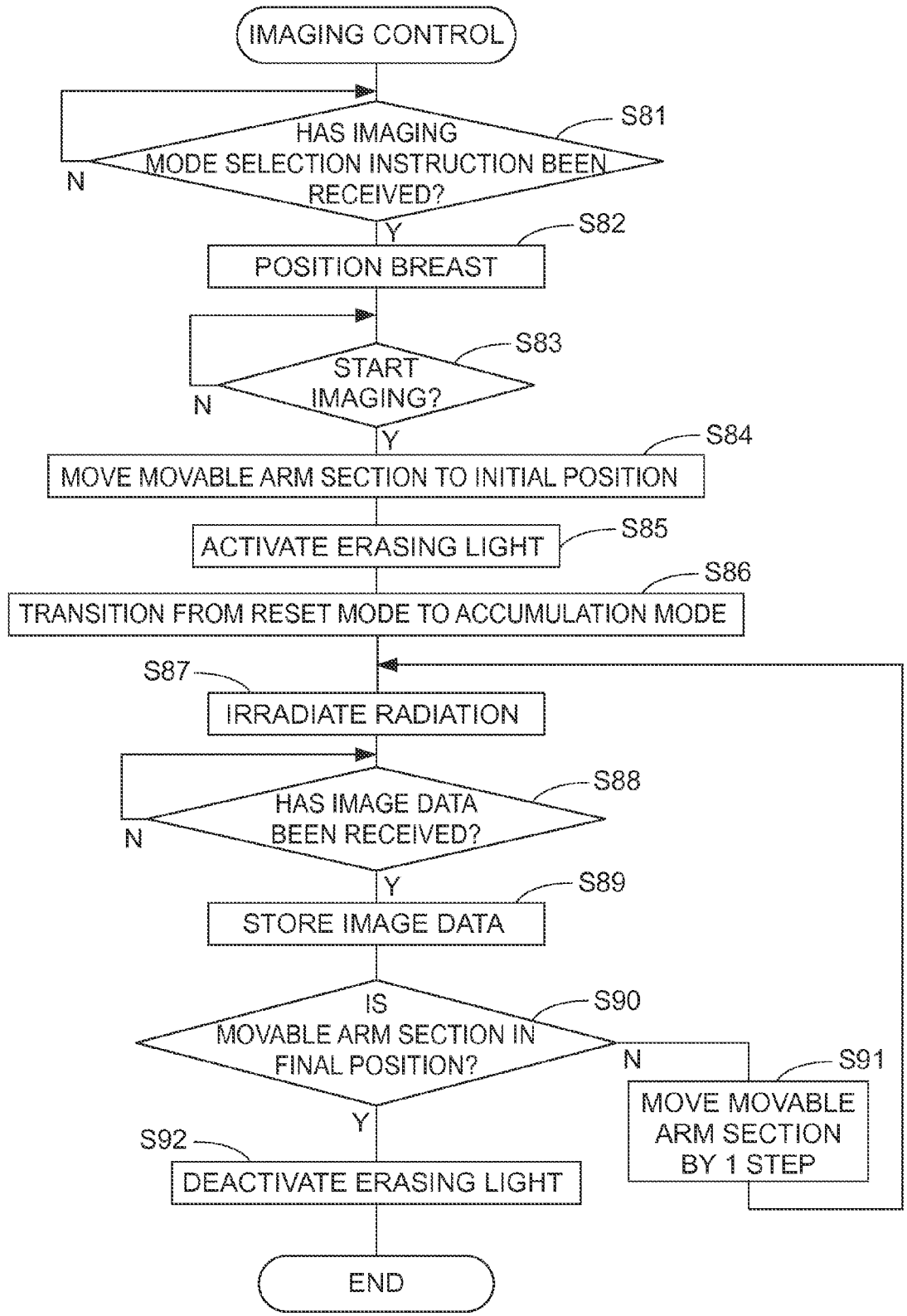

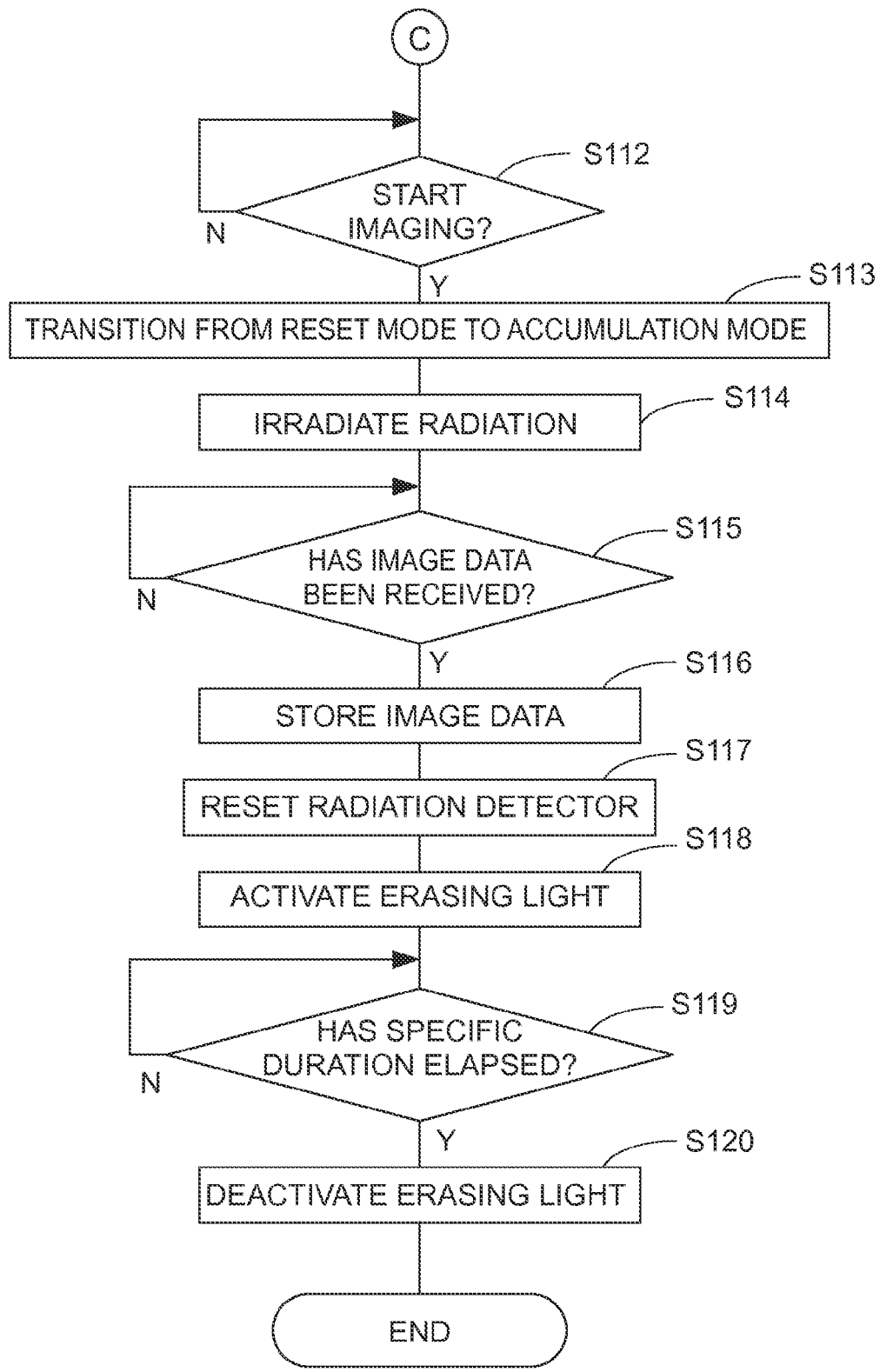

RADIATION IMAGE CAPTURE DEVICE, CONTROL METHOD FOR ERASING LIGHT SOURCE, AND COMPUTER-READABLE STORAGE MEDIUM

CROSS-REFERENCE TO RELATED APPLICATION

This application is based on and claims priority under 35 USC 119 from Japanese Patent Application No. 2013-209451 filed on Oct. 4, 2013, which is incorporated by reference herein.

BACKGROUND

Technical Field

The present invention relates to a radiation image capture device, a control method for an erasing light source, and a computer-readable storage medium.

Related Art

Known radiation image capture devices, such as mammography devices, are provided with a radiation detector (Flat Panel Detector: FPD) to perform X-ray imaging of a breast. Radiation detectors are classified into direct conversion method types and indirect conversion method types according to their different conversion methods. Direct conversion method type radiation detectors convert X-ray data directly into electrical signals in a photoconductor layer employing amorphous selenium (a-Se).

Direct conversion method type radiation detectors are capable of achieving both high sharpness and high sensitivity. However, it has been observed that radiation detectors employing amorphous selenium (a-Se) in the photoconductor layer are prone to lag images due to slow transportation of charges arising in the photoconductor layer. In order to erase such lag images, light (referred to below as erasing light) is illuminated toward the radiation detector to generate photoelectric charges inside the photoconductor layer, promoting the disappearance of residual charge remaining in the photoconductor layer.

For example, Japanese Patent Application Laid-Open (JP-A) No. 2009-11526 (Patent Publication 1) includes an imaging condition setting means that sets imaging conditions of X-rays irradiated from an X-ray tube, a light illuminating section that illuminates a backlight for erasing lag images in an X-ray detector, a voltage value setting means that sets a voltage value for the backlight illuminated by the light illuminating section, and an imaging condition-voltage value correspondence table that holds most appropriate backlight voltage values for erasing lag images, derived according to the imaging conditions set by the imaging condition setting means. The most appropriate backlight voltage value is extracted from the imaging condition-voltage value correspondence table according to the imaging conditions, the voltage value setting means changes to this backlight voltage value, and the backlight is illuminated.

Moreover, JP-A No. 2002-296713 (Patent Publication 2) describes a control method for causing photostimulated luminescence to be emitted by illuminating excitation light onto a photostimulable phosphor plate that has been formed with a latent image by radiation irradiated from a radiation source, and, after reading image data based on the photostimulated luminescence, erasing an lag image in a radiation image capture device by illuminating the photostimulable phosphor plate with erasing light after releasing. In cases in which imaging is performed plural times using the same photostimulable phosphor plate, an amount of radiation with which the photostimulable phosphor plate will be irradiated at the next imaging is predicted, and an illumination duration of the erasing light is varied.

Known mammography devices are installed with a tomosynthesis imaging function, in which plural projection images acquired by irradiating radiation from plural directions are reconstituted to generate tomosynthesis images. In tomosynthesis imaging, plural projection images are successively captured while sequentially switching the radiation irradiation direction.

In tomosynthesis imaging, it is not desirable to erase lag images by repeatedly switching an erasing light on and off in coordination with the radiation irradiation timings over plural shots, since offset variation occurs in image signals, causing variation in the density values of radiation images. Photoelectric charges arise in a photoconductive layer due to activating the erasing light, and although the photoelectric charges disappear naturally with deactivation of the erasing light, there is a delay in the generation and disappearance of the photoelectric charges with respect to the activation and deactivation timings of the erasing light. Accordingly, if the erasing light is repeatedly activated and deactivated at short cycles, charges inside the photoconductive layer does not attain a stable state, causing offset variation in image signals.

There is also an issue of non-uniformities arising in radiation images if radiation image capture is performed in an activated state of the erasing light. The photoelectric charge arising inside the photoconductive layer due to illumination with the erasing light is not uniform, due to such factors as unevenness in the layer thickness of the respective layers configuring the radiation detector. The non-uniformity of the photoelectric charges gives rise to the non-uniformities described above. In tomosynthesis imaging, in which the irradiation duration of one shot of radiation is comparatively short (for example approximately 100 msec), such non-uniformities are not liable to become an issue, however in two-dimensional (2D) imaging, in which the irradiation duration of radiation is longer than that of tomosynthesis imaging (for example approximately 1 to 6 seconds), such non-uniformities become pronounced.

SUMMARY

In consideration of the above points, an object of the present invention is to provide a radiation image capture device, a control method for an erasing light source, and a computer-readable storage medium that are capable of obtaining radiation images with better image quality than hitherto in both an imaging mode in which the radiation irradiation duration is comparatively short and radiation images are successively captured, and in an imaging mode in which the radiation irradiation duration is comparatively long.

A first aspect of the present invention provides a radiation image capture device including: a radiation source that irradiates radiation toward an imaging subject; a radiation detector that includes a sensor portion configured to generate charges according to radiation irradiated from the radiation source through the imaging subject, that reads charges generated in the sensor portion, and that generates image data of a radiation image; an erasing light source that illuminates the radiation detector with erasing light to erase charge remaining in the sensor portion; and a controller that, in a first imaging mode in which the radiation detector generates image data of a radiation image based on radiation irradiated from the radiation source over a first irradiation duration, places the erasing light source in a deactivated state at least from a start of radiation irradiation until completion of charge reading by the radiation detector, and that, in a second imaging mode in which the radiation detector generates image data of plural radiation images based on successively irradiated radiation from the radiation source over a second irradiation duration shorter than the first irradiation duration, places the erasing light source in an activated state for at least from a start of initial radiation irradiation until completion of final charge reading by the radiation detector.

A twelfth aspect of the present invention provides a non-transitory computer-readable storage medium stored with a program that causes a computer to function as the controller in the radiation image capture device of any one of the first aspect to the eleventh aspect.

A thirteenth aspect of the present invention provides a control method for an erasing light source in a radiation image capture device including a radiation source that irradiates radiation toward an imaging subject, a radiation detector that includes a sensor portion configured to generate charges according to radiation irradiated from the radiation source through the imaging subject, that reads charges generated in the sensor portion, and that generates image data of a radiation image, and an erasing light source that illuminates the radiation detector with erasing light to erase charge remaining in the sensor portion, the control method including: in a first imaging mode in which the radiation detector generates image data of a radiation image based on radiation irradiated from the radiation source over a first irradiation duration, placing the erasing light source in a deactivated state at least from a start of radiation irradiation until completion of charge reading by the radiation detector, and, in a second imaging mode in which the radiation detector generates image data of plural radiation images based on successively irradiated radiation from the radiation source over a second irradiation duration shorter than the first irradiation duration, placing the erasing light source in an activated state for at least from a start of initial radiation irradiation until completion of final charge reading by the radiation detector.

BRIEF DESCRIPTION OF THE DRAWINGS

An exemplary embodiment of the present invention will be described in detail based on the following figures, wherein:

FIG. 13A is a timing chart illustrating operation timings of respective sections of a radiation image capture device according to an exemplary embodiment of the present invention;

FIG. 13B is a timing chart illustrating operation timings of respective sections of a radiation image capture device according to an exemplary embodiment of the present invention;

FIG. 14 is a flowchart illustrating a processing flow in an imaging control program according to an exemplary embodiment of the present invention;

FIG. 15 is a flowchart illustrating a processing flow in an imaging control program according to an exemplary embodiment of the present invention;

FIG. 18 is a flowchart illustrating a processing flow in an imaging control program according to an exemplary embodiment of the present invention.

DETAILED DESCRIPTION

Figure 1:
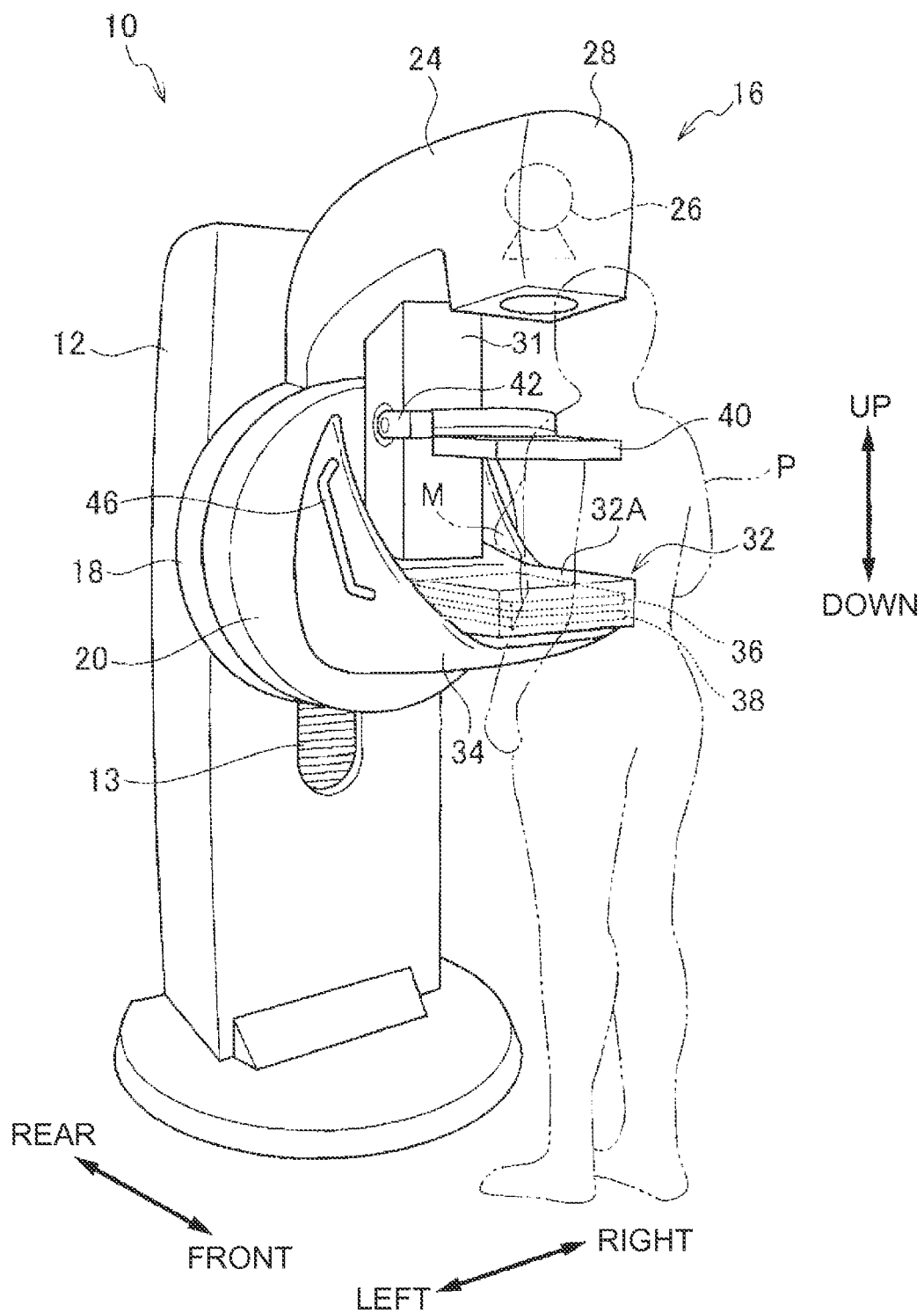
FIG. 1 is a perspective view illustrating a configuration of a mammography device according to an exemplary embodiment of the present invention.

Explanation follows regarding a mammography device according to an exemplary embodiment of the present invention, with reference to the drawings. Note that the same configuration elements are allocated the same reference numerals in each of the drawings.

First Exemplary Embodiment

Figure 2:
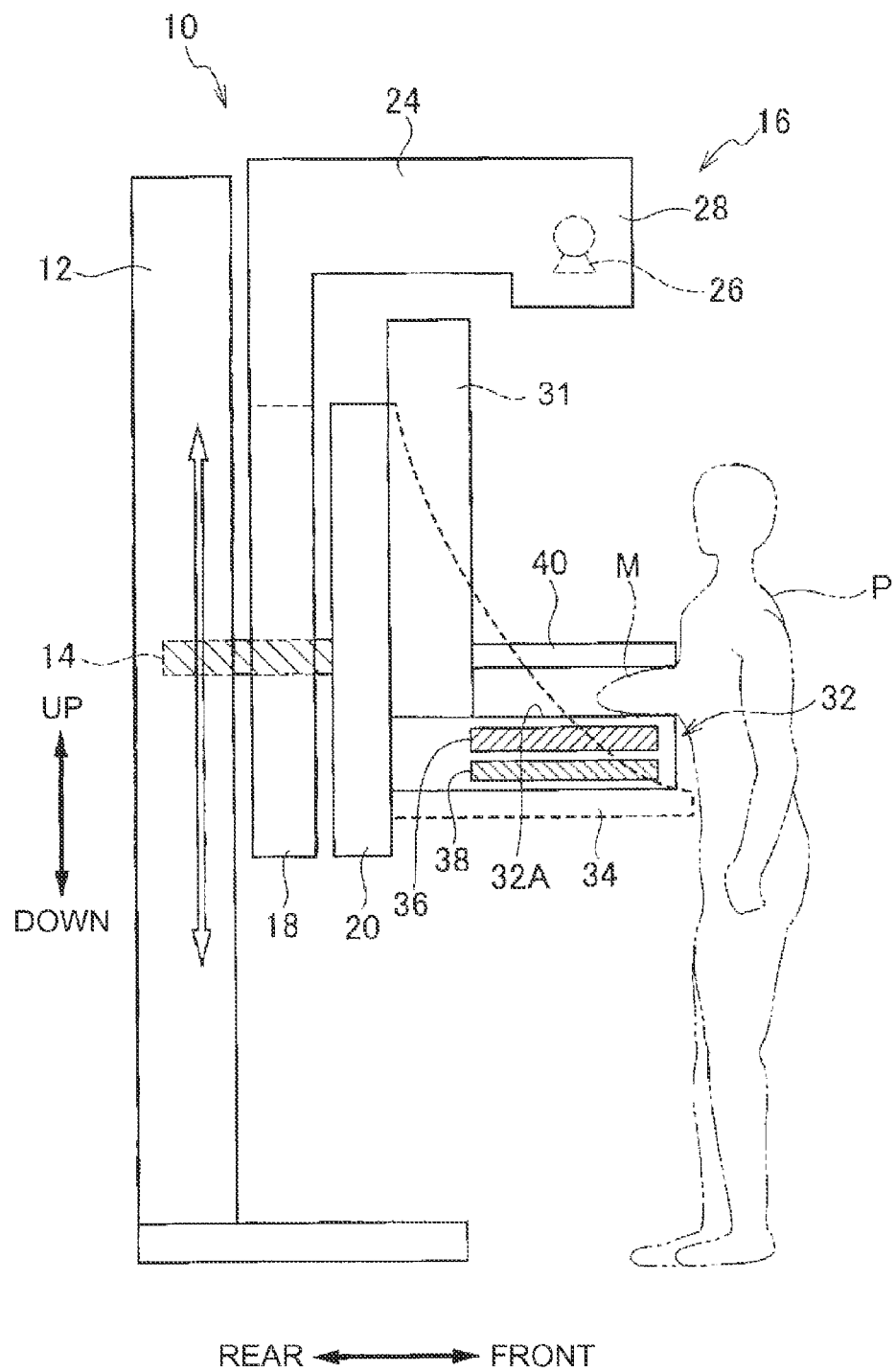
FIG. 2 is a cross-section of a mammography device according to an exemplary embodiment of the present invention.

FIG. 1 is a perspective view illustrating an example of a configuration of a radiation image capture device 10 according to an exemplary embodiment of the present invention. FIG. 2 is a cross-section of the radiation image capture device 10 according to an exemplary embodiment of the present invention, taken along a left-right direction center line. Note that the up-down direction, the left-right direction, and the front-rear direction refer to the directions from the perspective of a patient, serving as a subject P. The radiation image capture device 10 is a mammography device, and includes a base section 12, a rotation shaft 14 provided so as to be capable of moving along a guide portion 13 provided to the base section 12, and a movable arm section 16 attached to the rotation shaft 14. The movable arm section 16 is configured so as to be capable of moving in the up-down direction accompanying movement of the rotation shaft 14, and also configured so as to be capable of rotating toward the left and toward the right accompanying rotation of the rotation shaft 14.

The movable arm section 16 includes a first rotation portion 18 fixed to the rotation shaft 14, and a second rotation portion 20 that is coupled to the rotation shaft 14 so as to be capable of disengaging therefrom. The second rotation portion 20 is disposed on the subject P side of the first rotation portion 18. The rotation shaft 14 is fixed to the center of rotation of the first rotation portion 18, and is coupled to the center of rotation of the second rotation portion 20. The rotation shaft 14 and the second rotation portion 20 are, for example, both provided with gears, and the second rotation portion 20 is coupled to the rotation shaft 14 with the gears in an enmeshed state, and is disengaged from the rotation shaft 14 with the gears in a non-enmeshed state.

One end of an L-shaped support portion 24 is fixed to the first rotation portion 18. A radiation irradiation section 28 that irradiates radiation (X-rays) toward the breast M of the subject P is provided at the other end of the support portion 24. The radiation irradiation section 28 includes a radiation source 26 including an X-ray tube, and a radiation source driver 27 (see FIG. 6) that drives the radiation source 26 so as to irradiate radiation at a tube voltage value, tube current value, and irradiation duration according to an instruction from a main controller 50, described later. The radiation source 26 rotates about the rotation shaft 14 together with the first rotation portion 18 accompanying rotation of the rotation shaft 14.

A first retaining portion 31 that retains a press plate 40 is attached to the second rotation portion 20. The press plate 40 is supported so as to be capable of movement in the up-down direction by a support mechanism 42 attached to the first retaining portion 31. Lowering the press plate 40 presses the breast M of the subject P, fixing the breast M between an imaging face 32A and the press plate 40.

A second retaining portion 34 that retains an imaging table 32 is attached to the second rotation portion 20. The second retaining portion 34 is provided with a handle 46. The imaging table 32 includes the imaging face 32A that contacts the breast M of the subject P. A radiation detector 36 and an erasing light source 38 are housed inside the imaging table 32.

The radiation detector 36 is a direct conversion type FPD that detects radiation irradiated from the radiation source 26 through the breast M, and generates image data of a radiation image. Detailed explanation regarding configuration of the radiation detector 36 is given later.

The erasing light source 38 is provided at the back of the radiation detector 36 in the radiation irradiation direction, and illuminates erasing light toward the radiation detector 36 to erase charge remaining in a photoconducting section of the radiation detector 36 in response to a drive signal from an erasing light source driver 39 (see FIG. 6), described later. The erasing light source 38 is configured including, for example, a light guiding plate with a light emitting face disposed parallel to a detection face of the radiation detector 36, and a light source such as a light emitting diode (LED) provided at a side face of the light guiding plate. Note that the erasing light source may also be configured by disposing plural light sources such as LEDs in a two-dimensional pattern.

In a coupled state of the rotation shaft 14 and the second rotation portion 20, the radiation detector 36 and the erasing light source 38 housed in the imaging table 32 rotate about the rotation shaft 14 together with the second rotation portion 20 accompanying rotation of the rotation shaft 14. However, in a disengaged state of the rotation shaft 14 and the second rotation portion 20, the second rotation portion 20 does not rotate accompanying rotation of the rotation shaft 14, and the imaging table 32, the radiation detector 36 and the erasing light source 38 do not rotate. Namely, the radiation source 26 is capable of independent rotation with respect to the radiation detector 36 and the erasing light source 38.

As described above, the radiation image capture device 10 according to the present exemplary embodiment includes the movable arm section 16 that enables independent movement of the radiation irradiation section 28 and the radiation source 26 with respect to the imaging table 32 and the radiation detector 36. Various imaging modes, including craniocaudal imaging (CC imaging), mediolateral oblique imaging (MLO imaging), and tomosynthesis imaging, are accordingly possible.

Figure 3:
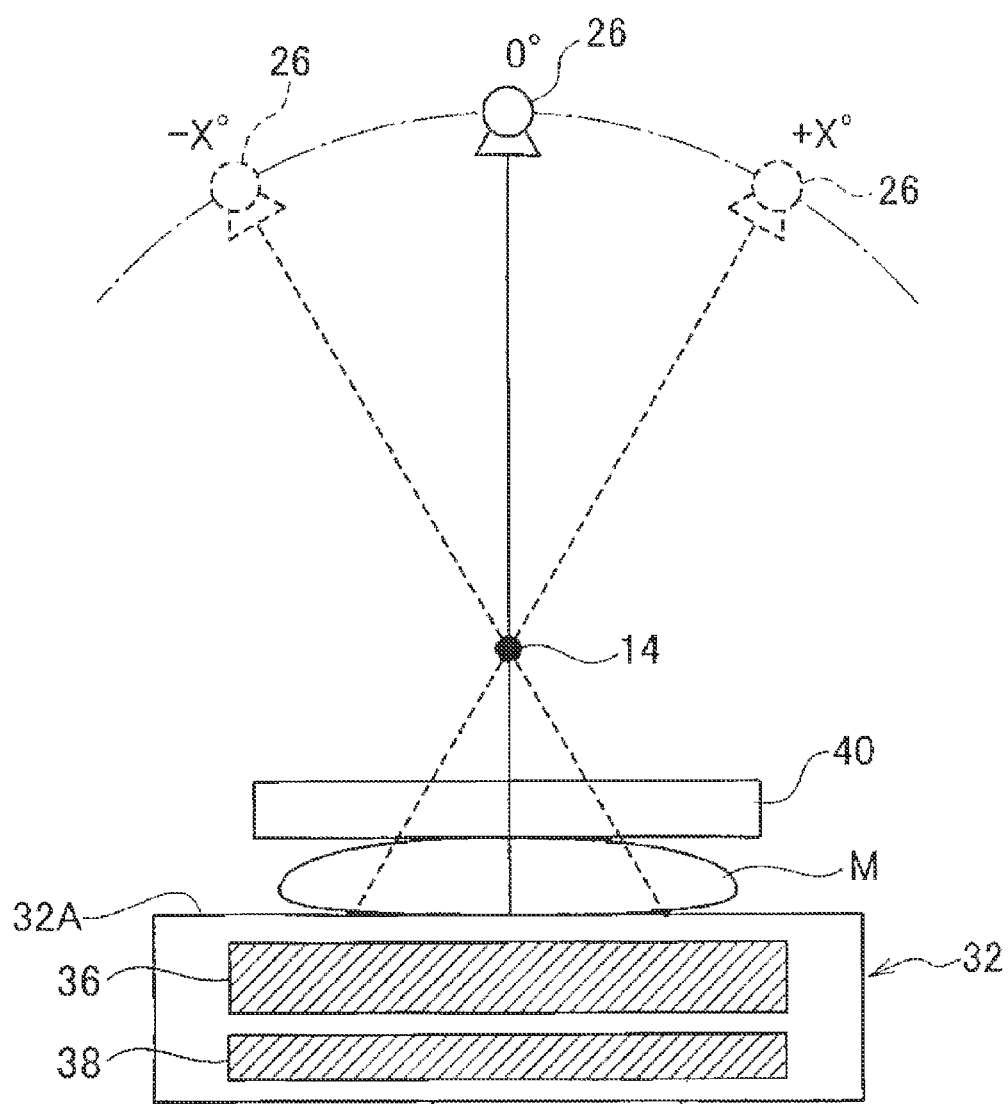
FIG. 3 is a schematic drawing to explain a tomosynthesis imaging function in a mammography device according to an exemplary embodiment of the present invention.

Explanation follows regarding a tomosynthesis imaging function of the radiation image capture device 10. FIG. 3 is a schematic drawing to explain the tomosynthesis imaging function of the radiation image capture device 10. Tomosynthesis imaging enables a tomographic image of the breast M to be reconstituted from plural projection images acquired by irradiating radiation toward the breast M, this being an imaging subject, from plural directions.

During tomosynthesis imaging of the subject P in a standing state, the imaging face 32A of the imaging table 32 is fixed in an upward-facing state, while radiation is irradiated from the radiation source 26 at plural irradiation angles by rotating the movable arm section 16 about the rotation shaft 14.

Rotating the movable arm section 16 about the rotation shaft 14 moves the radiation source 26 in a circular arc above the radiation detector 36, as illustrated in FIG. 3. For example, in cases in which rotation is in a positive direction, the radiation source 26 rotates toward the right by specific intervals, from an angle $-X°$ to an angle $+X°$. Note that a direction orthogonal to the imaging face 32A of the imaging table 32 (the detection face of the radiation detector 36) is defined as an irradiation angle $0°$.

In tomosynthesis imaging, the movable arm section 16 is rotated in a pressed state of the breast M, such that the angle position of the radiation source 26 moves with respect to the radiation detector 36 to irradiate radiation toward the breast M from plural directions and acquire plural projection images. A tomographic image is generated by reconstituting the plural projection images thus acquired.

Figure 4:
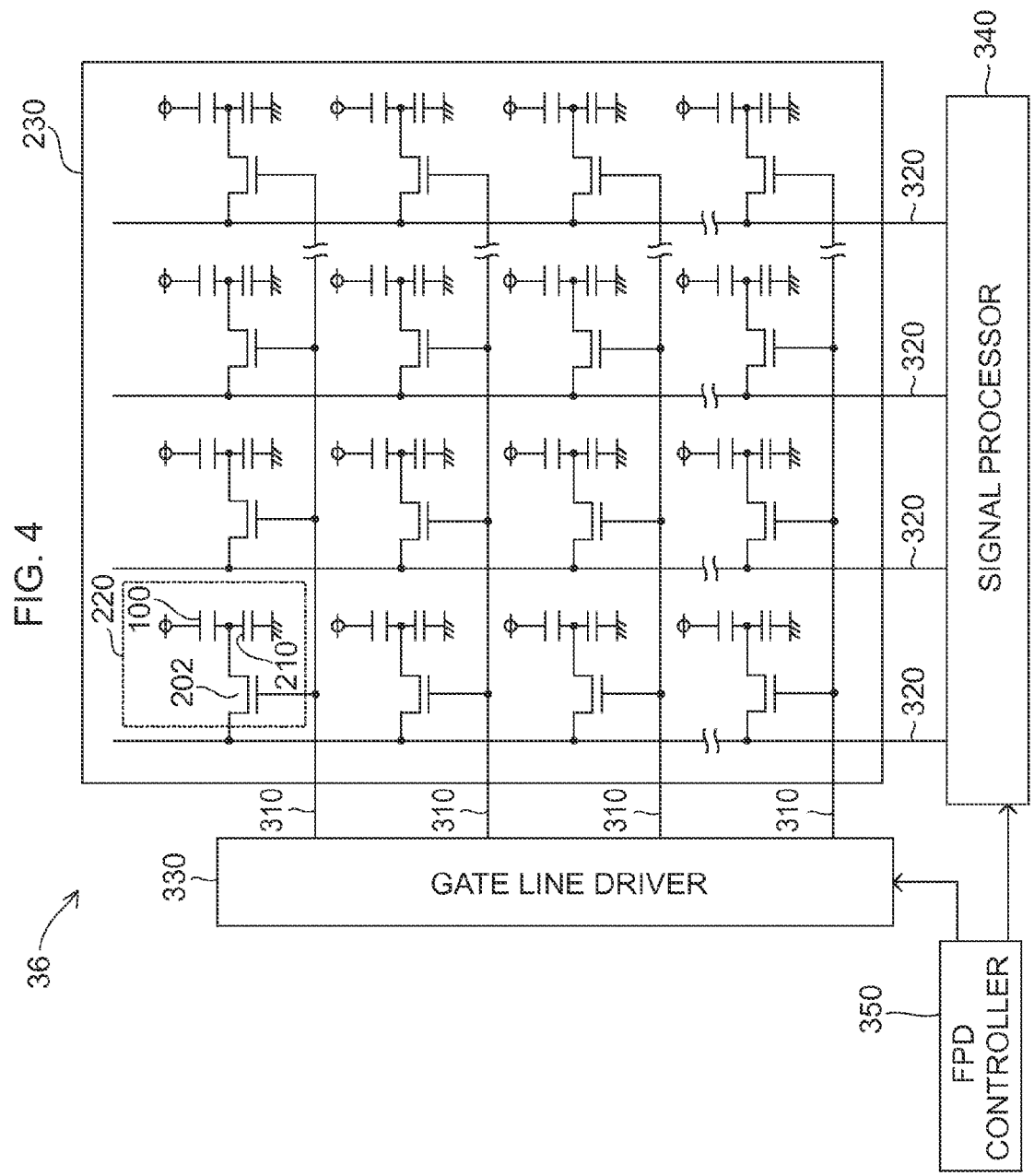
FIG. 4 is a circuit diagram of a radiation detector according to an exemplary embodiment of the present invention.

Next, explanation follows regarding configuration of the radiation detector 36. FIG. 4 is a circuit diagram of the radiation detector 36. The radiation detector 36 includes plural pixels 220, each including: a sensor portion 100 configured to generate charges from irradiated radiation; a capacitor 210 that accumulates charges generated in the sensor portion 100; and a switching element (for example a TFT 202) that reads the charges accumulated in the capacitor 210. The plural pixels 220 are disposed on a glass substrate 230 in a matrix formation. A bias voltage is applied to each sensor portion 100 through common wiring, not illustrated in the drawings. Note that the switching elements in the circuits of the radiation detector 36 are not limited to TFT type circuits, and may, for example, be CMOS type circuits.

Plural gate lines 310 that supply each of the TFTs 202 with gate signals to switch the respective TFTs 202 ON/OFF are provided on the glass substrate 230, the gate lines 310 extending in a specific direction (row direction) along the pixel 220 array. Plural signal lines 320 that transmit the charges accumulated in the capacitors 210 through the TFTs 202 in an ON state to a signal processor 340 are also provided on the glass substrate 230, the signal lines 320 extending in a direction (column direction) intersecting with the extension direction of the gate lines 310. The pixels 220 are each provided on the glass substrate 230 corresponding to respective intersection portions between the gate lines 310 and the signal lines 320.

Each of the gate lines 310 is connected to a gate line driver 330, and each of the signal lines 320 is connected to the signal processor 340. The TFTs 202 are placed in an ON state by gate signals supplied through the gate lines 310 from the gate line driver 330. The charges generated in the sensor portions 100 and accumulated in the capacitors 210 by placing the TFTs 202 in the ON state are read into the respective signal lines 320 as electric signals, and transmitted to the signal processor 340. The signal processor 340 processes the electric signals supplied through the signal lines 320 to generate image data of a radiation image.

An FPD controller 350 controls the gate line driver 330 and the signal processor 340 based on control signals from the main controller 50, described later, that performs overall control of operation of the radiation image capture device 10. The FPD controller 350 supplies control signals to the gate line driver 330 and the signal processor 340 to control output timings of gate signals output from the gate line driver 330, and to control signal processing timings in the signal processor 340.

Figure 5:
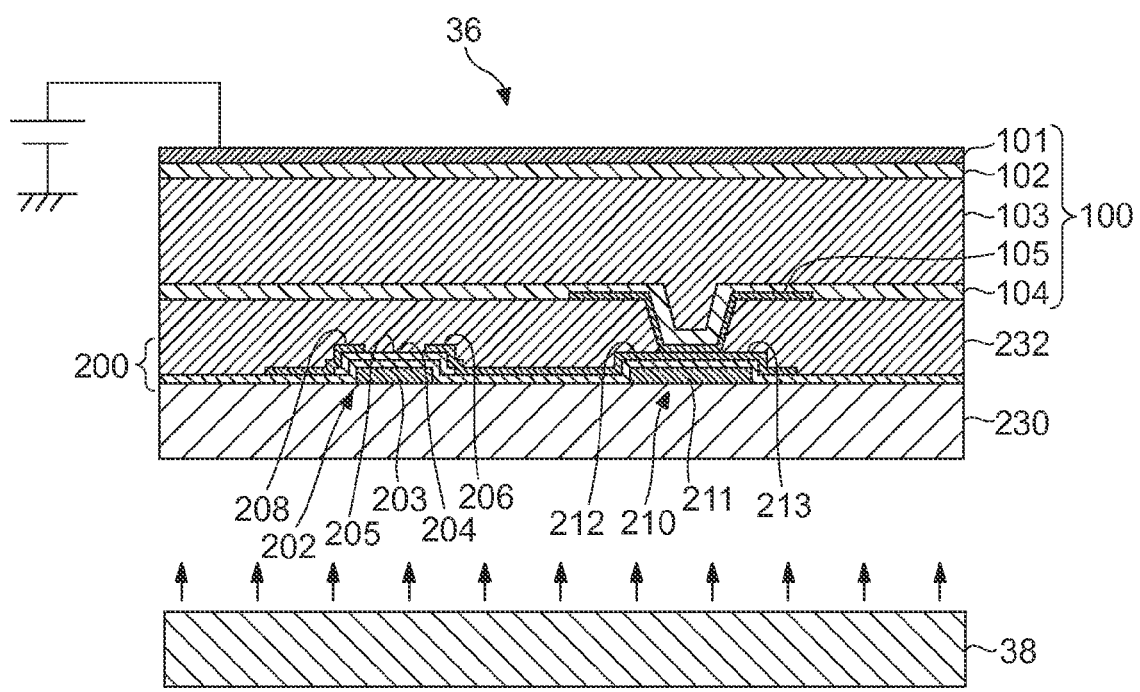
FIG. 5 is a cross-section of a radiation detector according to an exemplary embodiment of the present invention.

FIG. 5 is a cross-section illustrating configuration corresponding to a single pixel of the radiation detector 36. The radiation detector 36 includes the glass substrate 230, a charge reading section 200, including the TFTs 202 and the capacitors 210 formed on the glass substrate 230, and the sensor portions 100 provided over the charge reading section 200.

Each TFT 202 is configured including a gate electrode 203, a gate insulating film 204, a semiconductor layer 205, a source electrode 208, and a drain electrode 206. The gate electrode 203 is connected to the gate line 310 (see FIG. 4), the source electrode 208 is connected to the signal line 320 (see FIG. 4), and the drain electrode 206 is connected to an upper electrode 213 of the capacitor 210. The capacitor 210 is configured by layering a lower electrode 211, an insulating film 212, and the upper electrode 213. The insulating film 212 is integrally formed with the gate insulating film 204, and the upper electrode 213 is integrally formed with the drain electrode 206.

The sensor portions 100 are provided over the charge reading section 200 including the TFTs 202 and the capacitors 210, with an interlayer insulating film 232 interposed therebetween. Each sensor portion 100 is configured including a bias electrode 101, an electron transporting layer 102, a photoconductor layer 103, a hole transporting layer 104 and a charge collection electrode 105.

The photoconductor layer 103 generates charges on irradiation with X-rays. Amorphous selenium (a-Se), for example, has high dark-resistance, exhibits good electromagnetic conduction to X-rays, and is possible to form into a film of large surface area at a low temperature using a vacuum deposition method, and so may be suitably employed as the photoconductor layer 103.

The electron transporting layer 102 that prevents injection of holes while being a conducting body for electrons is provided over the photoconductor layer 103. $CeO_2$, $ZnS$, $Sb_2S_3$ or the like may be suitably employed for the electron transporting layer 102.

The bias electrode 101 that applies a bias voltage to the photoconductor layer 103 is provided over the electron transporting layer 102. Gold (Au) or the like may be employed in the bias electrode 101. In the present exemplary embodiment, a positive voltage is applied to the bias electrode 101.

The hole transporting layer 104 that prevents injection of electrons while being a conducting body for holes is provided below the photoconductor layer 103. $Sb_2S_3$, $CdS$, or Te doped Se, CdTe or the like may be suitably employed for the hole transporting layer 104.

The charge collection electrode 105, divided per pixel, is provided below the hole transporting layer 104. A semiconductor with high transmissivity to light, such as Indium-Tin-Oxide (ITO) or Indium-Zinc-Oxide (IZO) may be suitably employed as the charge collection electrode 105. The charge collection electrode 105 is connected to the upper electrode 213 of the capacitor 210 through a contact hole formed in the interlayer insulating film 232.

In the direct conversion type radiation detector 36 described above, when X-rays are incident to the photoconductor layer 103 that has been applied with a bias voltage through the bias electrode 101, the X-rays are absorbed in the photoconductor layer 103, generating electrons and holes. The generated electrons and holes are transported along an electrical field arising inside the photoconductor layer 103. Due to the electrical field, the holes are collected in the charge collection electrode 105, and accumulated in the capacitor 210.

When the TFTs 202 are placed in an ON state by the gate signal supplied through the gate lines 310 from the gate line driver 330, the charges collected in the capacitors 210 are read into the respective signal lines 320, and transmitted to the signal processor 340. The signal processor 340 generates a radiation image based on the electric signals supplied through the respective signal lines 320.

FIG. 5 illustrates the radiation detector 36 together with the erasing light source 38. The erasing light source 38 is disposed on the glass substrate 230 side of the radiation detector 36. Erasing light illuminated from the erasing light source 38 illuminates the photoconductor layer 103 through the glass substrate 230, the charge reading section 200, and the interlayer insulating film 232. Photoelectric charges are generated in the photoconductor layer 103 due to illuminating the photoconductor layer 103 with the erasing light. As the photoelectric charges move along the electrical field arising inside the photoconductor layer 103, residual charge remaining inside the photoconductor layer 103 is eliminated. A lag image caused by the residual charge is thereby erased.

Figure 6:
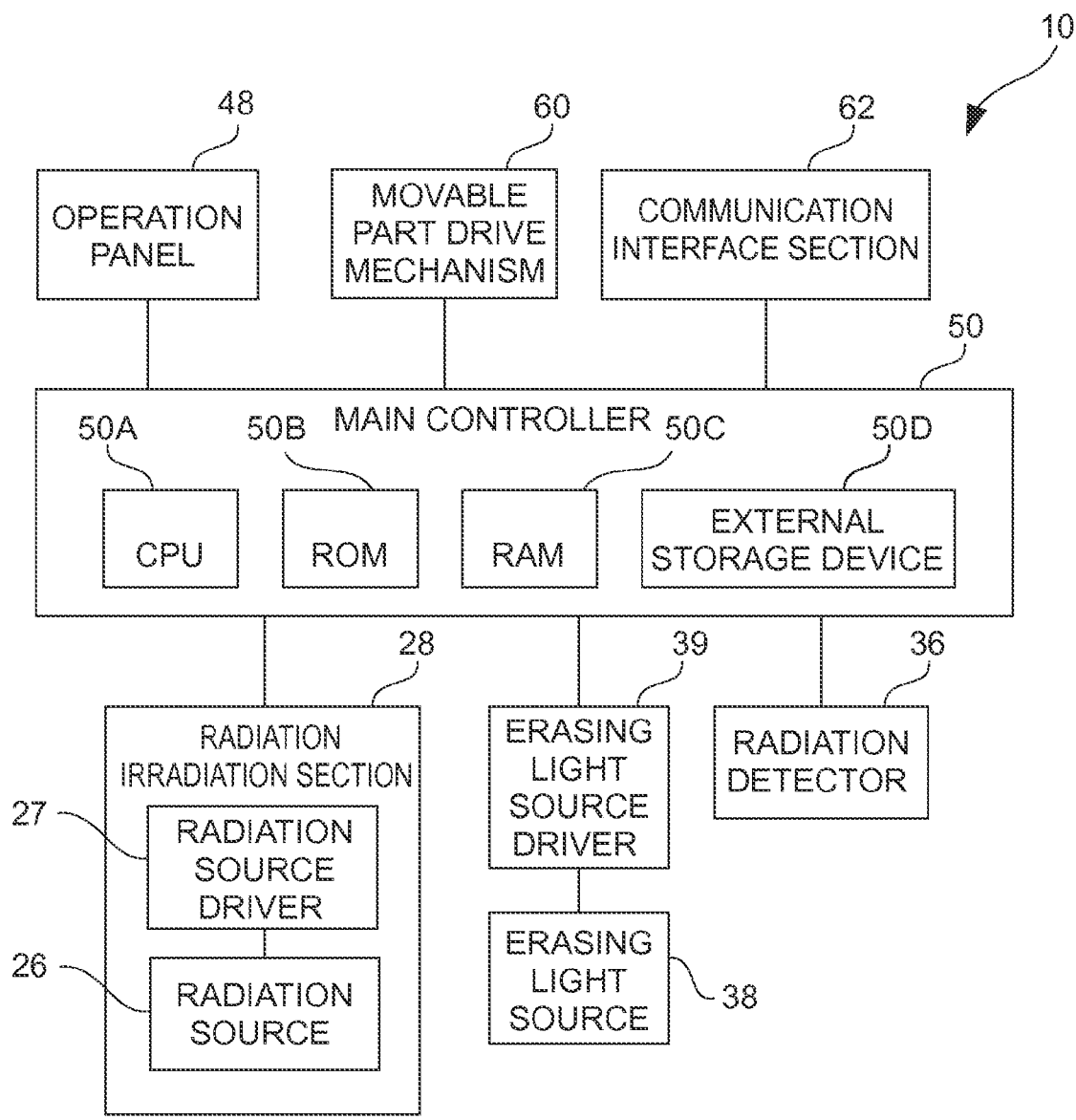
FIG. 6 is a block diagram of a radiation image capture device according to an exemplary embodiment of the present invention.

FIG. 6 is a block diagram illustrating a control configuration of the radiation image capture device 10. The radiation image capture device 10 includes the radiation irradiation section 28 provided with the radiation source 26 and the radiation source driver 27, the radiation detector 36, the erasing light source 38, the erasing light source driver 39, and an operation panel 48. The radiation image capture device 10 further includes the main controller 50 that controls overall operation of the device, a movable part drive mechanism 60 that drives movable parts such as the rotation shaft 14, the movable arm section 16, and the press plate 40 during imaging, and a communication interface section 62 that is connected to a network such as a Local Area Network (LAN) and performs transmission and reception of various data between the radiation image capture device 10 and other devices connected to the network.

The main controller 50 includes a central processing unit (CPU) 50A, Read Only Memory (ROM) 50B, Random Access Memory (RAM) 50C, and a non-volatile external storage device 50D such as a Hard Disk Drive (HDD). The main controller 50 is respectively connected to the radiation irradiation section 28, the radiation detector 36, the erasing light source driver 39, the operation panel 48, the movable part drive mechanism 60, and the communication interface section 62. The ROM 50B is stored with various programs, various data, and the like utilized by the CPU 50A.

The radiation source driver 27, the radiation detector 36, the erasing light source driver 39 and the movable part drive mechanism 60 are operated based on control signals supplied from the main controller 50. Namely, the radiation source driver 27 drives the radiation source 26 so as to irradiate radiation at a specific tube voltage, tube current, and irradiation duration based on control signals supplied from the main controller 50. The FPD controller 350 of the radiation detector 36 controls the gate line driver 330 and the signal processor 340 based on control signals supplied from the main controller 50, and also controls timings for accumulating and reading charges arising in the sensor portions 100. The erasing light source driver 39 controls timings for activating and deactivating the erasing light source 38 based on control signals supplied from the main controller 50. The movable part drive mechanism 60 drives movable parts such as the rotation shaft 14, the movable arm section 16, and the press plate 40 based on control signals supplied from the main controller 50.

The operation panel 48 notifies the main controller 50 with data indicating an imaging mode selected according to an input operation of the operation panel 48 by a user. Note that the operation panel 48 may be provided as part of radiation image capture device 10, or may be provided in a control board that is separate to the radiation image capture device 10 and capable of communication with the radiation image capture device 10.

Explanation follows regarding operation of the radiation image capture device 10 according to an exemplary embodiment of the present invention during radiation image capture. The following explanation describes a case in which a series of radiation images are acquired in an imaging sequence of performing tomosynthesis imaging, in which radiation is successively irradiated at plural different irradiation angles to acquire plural radiation images, and after the tomosynthesis imaging, performing two-dimensional (2D) imaging in which radiation is irradiated at a specific irradiation angle to acquire a radiation image.

Figure 7:
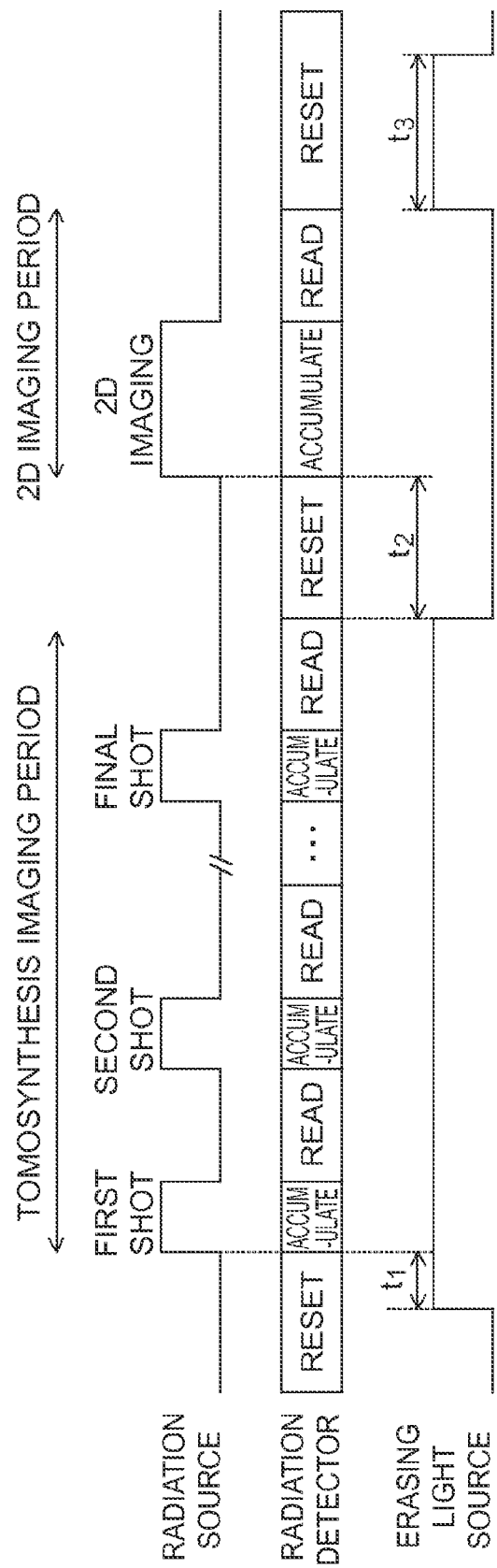
FIG. 7 is a timing chart illustrating operation timings of respective sections of a radiation image capture device according to an exemplary embodiment of the present invention.

FIG. 7 is a timing chart illustrating operation timings of respective sections of the radiation image capture device 10 in a case in which tomosynthesis imaging is performed first, followed by 2D imaging after the tomosynthesis imaging. FIG. 7 illustrates irradiation timings for irradiating radiation from the radiation source 26, operation modes of the radiation detector 36, and timings for activating and deactivating the erasing light source 38. In the chart illustrating radiation irradiation timings in the top row of FIG. 7, the high level corresponds to radiation irradiation, and the low level corresponds to radiation non-irradiation. In the chart illustrating timings for activation and deactivation of the erasing light source in the bottom row of FIG. 7, the high level corresponds to activation of the erasing light, and the low level corresponds to deactivation of the erasing light (this also applies to FIG. 10, FIG. 13A, FIG. 13B, and FIG. 16).

In a period prior to starting the initial radiation irradiation (the first shot) of tomosynthesis imaging, the radiation detector 36 resets each of the pixels 220. Reset refers to processing in which the TFTs 202 are switched ON to discharge charges resulting from dark current that have accumulated in the capacitors 210 of the radiation detector 36 into the signal lines 320. In a reset mode, the radiation detector 36 outputs gate signals from the gate line driver 330 to each of the gate lines 310 in sequence, switching ON the TFTs 202 connected to each of the gate lines 310 in sequence, to discharge the accumulated charges in the capacitors 210. The radiation detector 36 stops the reset mode prior to starting the first shot.

The erasing light source 38 transitions to an activated state at a timing prior to the start of the first shot. In the present exemplary embodiment, a duration of 1 second or longer is secured for a period $t_1$ from the start of erasing light source 38 activation until the first shot is started. The erasing light source 38 maintains the activated state throughout the period of tomosynthesis imaging (until the charges have been read for the final shot).

At a timing for performing the first shot, the radiation detector 36 transitions to an accumulation mode in which charges generated in the sensor portions 100 accompanying radiation irradiation are accumulated in the capacitors 210 of the respective pixels 220. In the accumulation mode, the radiation detector 36 places the TFTs 202 of each of the pixels 220 in an OFF state. Note that in the present exemplary embodiment, the irradiation duration (charge accumulation duration in the radiation detector 36) of a single time of radiation in tomosynthesis imaging is approximately 100 msec. The radiation irradiation duration may be set as appropriate according to the imaging subject.

At a timing of the end of the first shot of radiation, the radiation detector 36 transitions to a read mode for reading the charges accumulated in the respective capacitors 210 of the pixels 220. In the read mode, the radiation detector 36 outputs gate signals from the gate line driver 330 to each of the gate lines 310 in sequence, placing the TFTs 202 connected to each of the gate lines 310 in an ON state in sequence. The accumulated charges in the capacitors 210 are accordingly read into the signal lines 320. The read charges are supplied to the signal processor 340, and image data is generated for a radiation image corresponding to the irradiation angle.

When charge reading has been completed following the first shot, radiation irradiation is performed for a second time (a second shot) at a different irradiation angle to the first shot. Similarly to in the first shot, the radiation detector 36 transitions to the accumulation mode at a timing of radiation irradiation start, and transitions to the read mode at a timing of radiation irradiation end. Radiation irradiation is subsequently performed plural times whilst varying the radiation irradiation angle in sequence, with the radiation detector 36 repeating charge accumulation and reading in coordination with the radiation irradiation timings.

The erasing light source 38 transitions to a deactivated state at a timing of charge reading completion following the final shot when the final radiation irradiation (the final shot) of tomosynthesis imaging has been performed. Namely, the erasing light source 38 maintains the activated state throughout the period from prior to starting the first shot until charge reading has been completed following the final shot. The disappearance of residual charge arising in the sensor portions 100 at each shot is accordingly achieved, erasing lag images at each shot.

When tomosynthesis imaging has ended, the radiation detector 36 transitions to the reset mode, and the TFTs 202 connected to each of the gate lines 310 are switched ON in sequence to discharge the accumulated charges in the capacitors 210. Note that in the present exemplary embodiment, an example is described in which the erasing light source 38 transitions to the deactivated state at a timing of charge reading completion following the final shot in tomosynthesis imaging, however the erasing light source 38 may transition to the deactivated state during the reset period after the end of tomosynthesis imaging.

Transition is made to 2D imaging when reset has been completed for each of the pixels 220 in the radiation detector 36. The radiation detector 36 transitions to the accumulation mode at a timing of radiation irradiation for 2D imaging. In the present exemplary embodiment, a duration of 1 second or longer is secured for a period $t_2$ from transition of the erasing light source 38 to the deactivated state accompanying the end of tomosynthesis imaging until the start of radiation irradiation for 2D imaging. In the present exemplary embodiment, the irradiation duration (charge accumulation duration in the radiation detector 36) for an exposure in 2D imaging is longer than the irradiation duration in tomosynthesis imaging, at approximately 1 to 6 seconds. The radiation irradiation duration may be set as appropriate according to the imaging subject. The erasing light source 38 maintains the deactivated state during charge accumulation for 2D imaging by the radiation detector 36.

The radiation detector 36 transitions to the read mode at a timing of the end of radiation irradiation for 2D imaging. Image data is accordingly generated for a radiation image by 2D imaging. The erasing light source 38 maintains the deactivated state during charge reading by the radiation detector 36.

The radiation detector 36 transitions to the reset mode on completion of charge reading, and the TFTs 202 connected to each of the gate lines 310 are switched ON in sequence to discharge the accumulated charges in the capacitors 210. The erasing light source 38 transitions to the activated state at a timing of charge reading completion. The erasing light source 38 maintains the activated state over a period $t_3$ that is sufficient for an lag image due to the 2D imaging to be erased (for example 5 seconds), after which the erasing light source 38 transitions to the deactivated state.

In the radiation image capture device 10 according to the present exemplary embodiment, the erasing light source 38 accordingly maintains the activated state during successive acquisition of plural radiation images while switching the radiation irradiation angle in the tomosynthesis imaging mode. Lag images arising at each radiation image capture can accordingly be erased. In tomosynthesis imaging, image non-uniformities are not liable to occur even in cases in which imaging is performed in an illuminated state of the erasing light, since the irradiation duration of one shot is approximately 100 msec, this being much shorter than that during 2D imaging (approximately 1 to 6 seconds).

Offset variation in the radiation detector 36 can be prevented since the erasing light is not switched on and off in coordination with the radiation irradiation timings over plural shots.

Moreover, charges in the sensor portions 100 of the radiation detector 36 can attain a stable state by the point when tomosynthesis imaging starts since the erasing light source 38 transitions to the activated state prior to the start of tomosynthesis imaging. A certain amount of time is required for charges in the photoconductor layer 103 to attain a stable state after transition of the erasing light source 38 to the activated state or the deactivated state. In the present exemplary embodiment, a duration of 1 second or longer is secured for the period $t_1$ from transition of the erasing light source 38 to the activated state until the first shot is performed, thereby enabling charges in the sensor portions 100 of the radiation detector 36 to attain a stable state by the time of transition to the accumulation mode. Offset variation can accordingly be even more effectively prevented. Note that, within a range for which a tolerable amount of offset variation, the period $t_1$ may be set to a shorter period or a longer period than 1 second.

In 2D imaging, the radiation irradiation duration is comparatively long, at approximately 1 to 6 seconds, and there is a concern of image non-uniformities arising if the radiation detector 36 is illuminated with erasing light during 2D imaging. In the radiation image capture device 10 according to the present exemplary embodiment, the erasing light source 38 maintains the deactivated state throughout radiation irradiation for 2D imaging, and the accumulation and reading of charges in the radiation detector 36, enabling non-uniformities to be prevented from occurring in the radiation image acquired in 2D imaging.

Moreover, charges in the sensor portions 100 of the radiation detector 36 can attain a stable state by the point when 2D imaging starts, since the erasing light source 38 transitions to the deactivated state prior to the start of 2D imaging. In the present exemplary embodiment, a duration of 1 second or longer is secured for the period $t_2$ from transition of the erasing light source 38 to the deactivated state after the end of tomosynthesis imaging until the start of 2D imaging. Charges in the sensor portions 100 of the radiation detector 36 can accordingly attain a stable state at the transition to the accumulation mode during 2D imaging, and offset variation in 2D imaging can be prevented. Note that, within a range for which a tolerable amount of offset variation, the period $t_2$ may be may be set to a period longer or shorter than 1 second, and may be modified as appropriate in consideration of the transition period from the tomosynthesis imaging mode to the 2D imaging mode, for example. The period $t_2$ can be maximized due to the erasing light source 38 transitioning to the deactivated state at the point of charge reading completion following the final shot in tomosynthesis imaging, as in the present exemplary embodiment.

A lag image can be reliably erased due to securing a duration of approximately 5 seconds for the period $t_3$ of the activated state of the erasing light source 38 after completion of charge reading in 2D imaging. Note that it is sufficient to secure an adequate duration to erase the lag image for the period $t_3$, and a shorter duration or a longer duration than 5 seconds may be set. Moreover, when a sufficient duration to allow residual charge remaining in the sensor portions 100 to disappear naturally is secured after 2D imaging, activation of the erasing light source 38 after 2D imaging may be omitted.

Figure 8:
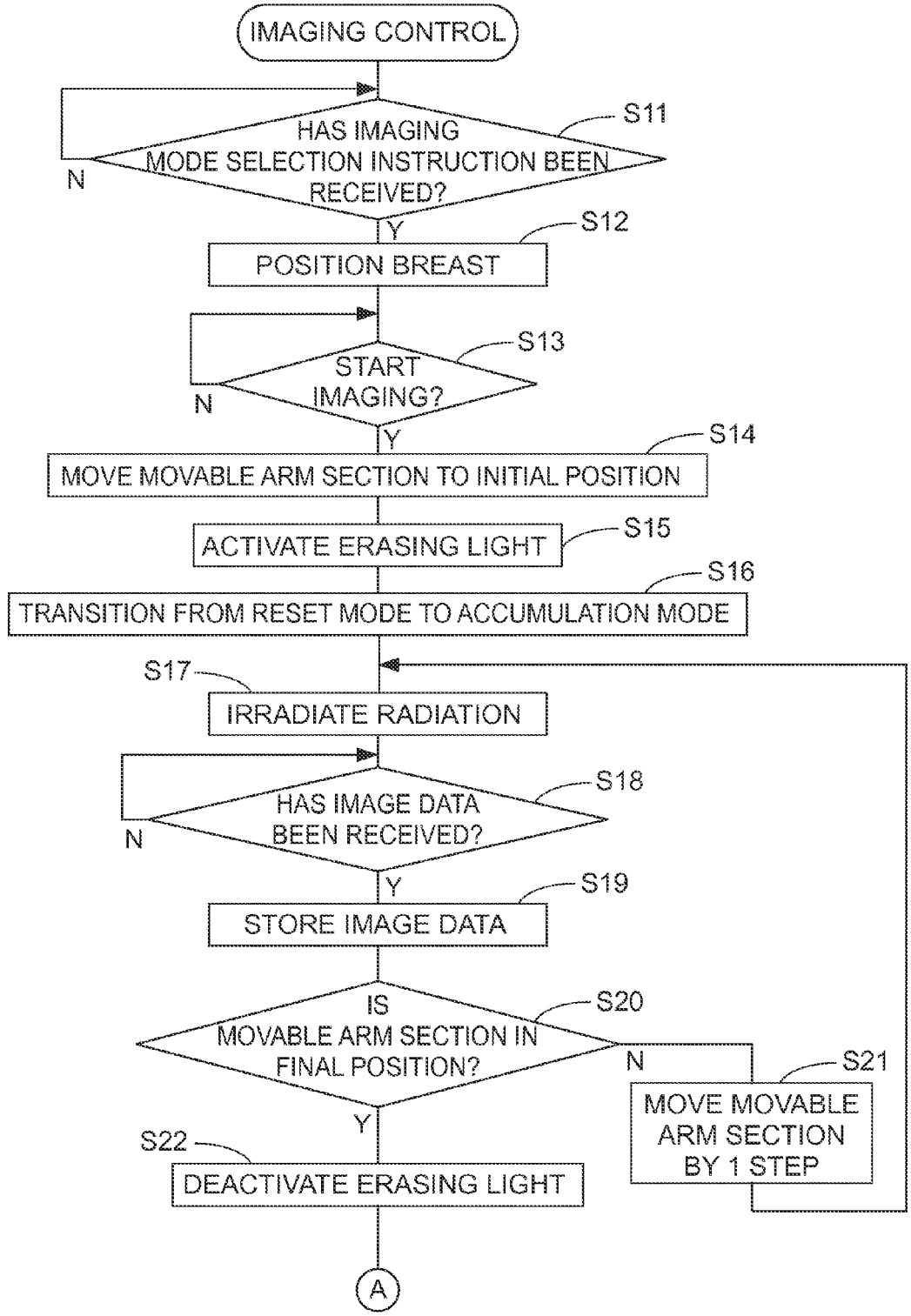
FIG. 8 is a flowchart illustrating a processing flow in an imaging control program according to an exemplary embodiment of the present invention.
Figure 9:
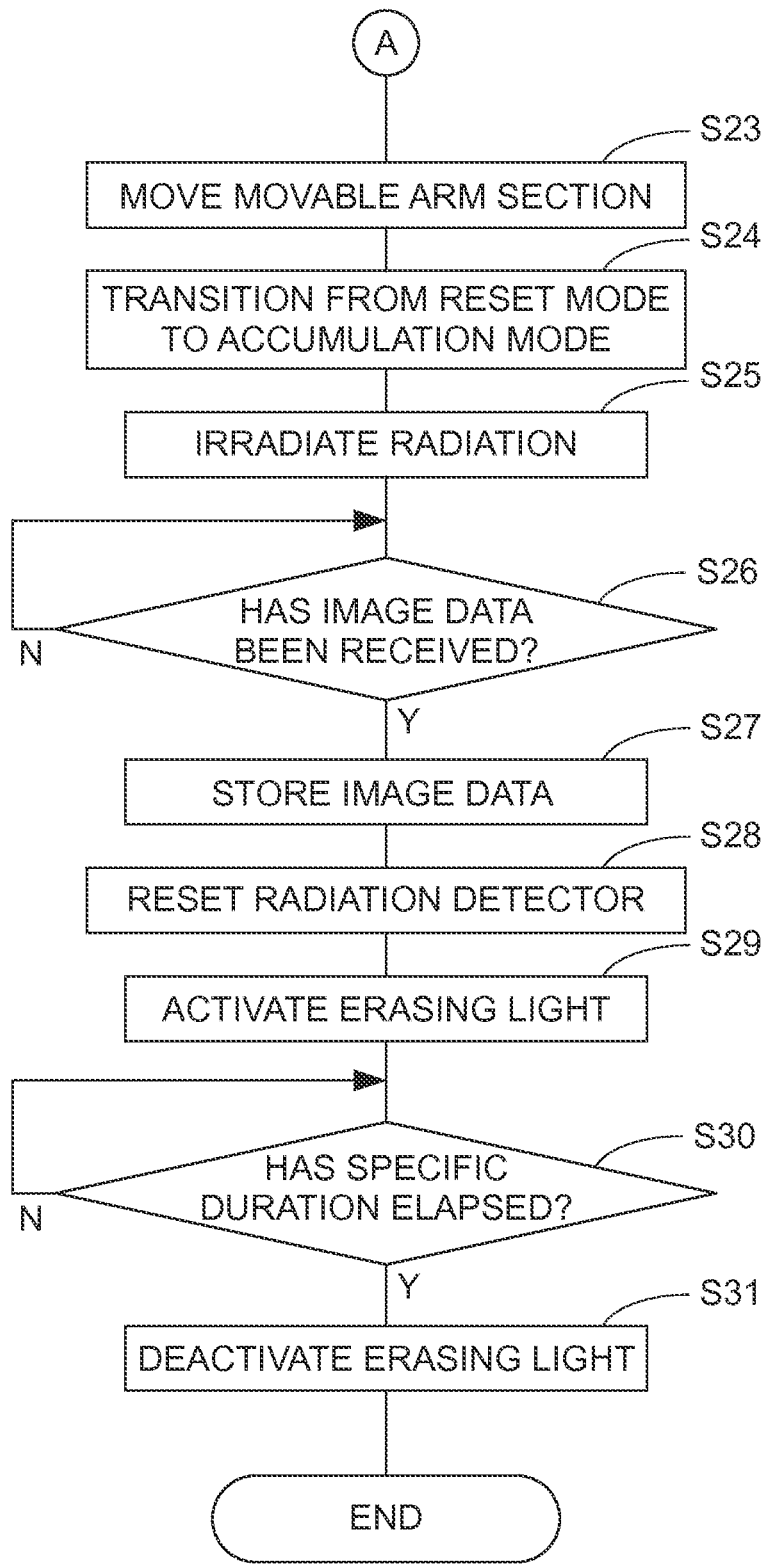
FIG. 9 is a flowchart illustrating a processing flow in an imaging control program according to an exemplary embodiment of the present invention.

FIG. 8 and FIG. 9 are flowcharts illustrating a processing flow of an imaging control program executed by the CPU 50A configuring the main controller 50. The imaging control program is stored in the ROM 50B. The flowcharts in FIG. 8 and FIG. 9 correspond to the timing chart illustrated in FIG. 7. Note that the erasing light source 38 is in the deactivated state at the point when execution of the imaging control program starts.

At step S11, the CPU 50A performs reception standby for an imaging mode selection instruction. A user is able to perform imaging mode selection by operating the operation panel 48. Note that here, an imaging mode is selected in which tomosynthesis imaging, in which radiation is successively irradiated from plural directions to acquire plural radiation images, is followed by 2D imaging, in which radiation is irradiated from a single direction to acquire a single radiation image. Processing transitions to step S12 when the CPU 50A has received an imaging mode selection instruction from the operation panel 48.

At step S12, the breast M is positioned with respect to the imaging table.

At step S13, the CPU 50A determines whether or not tomosynthesis imaging start has been instructed. Processing transitions to step S14 when the user has, for example, operated an imaging button (not illustrated in the drawings) to instruct tomosynthesis imaging start.

At step S14, the CPU 50A transmits a control signal to the movable part drive mechanism 60 to move a rotation angle position of the movable arm section 16 to an initial position. The movable part drive mechanism 60 that has received the control signal from the CPU 50A moves the movable arm section 16 to a rotation angle position of maximum tilt (the −X° position in FIG. 3), for example.

At step S15, the CPU 50A transmits a control signal to the erasing light source driver 39 to start activation of the erasing light. The erasing light source driver 39 that has received the control signal from the CPU 50A supplies a drive signal to the erasing light source 38, placing the erasing light source 38 in the activated state. The radiation detector 36 is accordingly illuminated with erasing light.

At step S16, the CPU 50A notifies the FPD controller 350 of the radiation detector 36 that radiation irradiation preparation has been completed. On receipt of notification from the CPU 50A that radiation irradiation preparation has been completed, the FPD controller 350 of the radiation detector 36 transitions from the reset mode, in which accumulated charges are removed from the respective capacitors 210 of the pixels 220, to the accumulation mode.

At step S17, the CPU 50A supplies the radiation source driver 27 with a control signal for starting radiation irradiation for tomosynthesis imaging. The radiation source driver 27 that has received the control signal from the CPU 50A drives the radiation source 26 to perform radiation irradiation under specific irradiation conditions. Radiation is accordingly irradiated from the radiation source 26 toward the breast M. Note that the radiation irradiation duration at step S17 is approximately 100 msec. The radiation irradiates the radiation detector 36 through the breast M. The radiation detector 36 transitions to the accumulation mode and the read mode in coordination with the radiation irradiation timing, generating image data for a radiation image corresponding to the radiation intensity distribution of the irradiated radiation that has passed through the breast M. The generated image data is transmitted to the CPU 50A.

At step S18, the CPU 50A performs standby for image data receipt from the radiation detector 36, and when the image data has been received from the radiation detector 36, processing transitions to step S19. At step S19, the CPU 50A stores the acquired image data in the external storage device 50D.

At step S20, the CPU 50A determines whether or not the rotation angle position of the movable arm section 16 is at the final position (the +X° position in the present exemplary embodiment). Processing transitions to step S21 if the CPU 50A determines that the movable arm section 16 is not at the final position, and processing transitions to step S22 if the CPU 50A determines that the movable arm section 16 is at the final position.

At step S21, the CPU 50A transmits a control signal to the movable part drive mechanism 60 to move the rotation angle position of the movable arm section 16 by one step in the positive direction. The movable part drive mechanism 60 that has received the control signal from the CPU 50A moves the rotation angle position of the movable arm section 16 by one step in the positive direction. When the movement of the movable arm section 16 is complete, the CPU 50A repeats the processing of step S17 to step S21. Radiation is accordingly irradiated plural times while moving the movable arm section 16 from −X° to +X°, image data is acquired for each angle position of the movable arm section 16, and the acquired image data is respectively stored in the external storage device 50D.

At step S22, the CPU 50A transmits a control signal to the erasing light source driver 39 to deactivate the erasing light. The erasing light source driver 39 that has received the control signal from the CPU 50A places the erasing light source 38 in the deactivated state. Tomosynthesis imaging has been completed by the respective processing described above, and transition is made to 2D imaging.

At step S23, the CPU 50A transmits a control signal to the movable part drive mechanism 60 to move the rotation angle position of the movable arm section 16 to a specific position for performing 2D imaging. The movable part drive mechanism 60 that has received the control signal from the CPU 50A moves the movable arm section 16 to the specific position for performing 2D imaging. The angle position of the movable arm section 16 in 2D imaging may be the angle position where the radiation irradiation direction is orthogonal to the detection face of the radiation detector 36. Note that 2D imaging may also be performed from the angle position of the final shot in tomosynthesis imaging. In such cases, the processing of step S23 may be omitted.

At step S24, the CPU 50A notifies the FPD controller 350 of the radiation detector 36 that radiation irradiation preparation for 2D imaging has been completed. On receipt of notification from the CPU 50A that radiation irradiation preparation has been completed, the FPD controller 350 of the radiation detector 36 transitions from the reset mode, in which accumulated charges are removed from the respective capacitors 210 of the pixels 220, to the accumulation mode.

At step S25, the CPU 50A transmits a control signal to the radiation source driver 27 to start radiation irradiation for 2D imaging. The radiation source driver 27 that has received the control signal from the CPU 50A drives the radiation source 26 to irradiate radiation under specific irradiation conditions. Radiation is accordingly irradiated from the radiation source 26 toward the breast M. Note that the radiation irradiation duration at step S25 is longer than the radiation irradiation duration during tomosynthesis imaging, at approximately 1 to 6 seconds. The radiation irradiates the radiation detector 36 through the breast M. The radiation detector 36 transitions to the accumulation mode and the read mode in coordination with the radiation irradiation timing, generating image data for a radiation image corresponding to the radiation intensity distribution of the irradiated radiation that has passed through the breast M. The generated image data is transmitted to the CPU 50A.

At step S26, the CPU 50A performs standby for image data receipt from the radiation detector 36, and processing transitions to step S27 when the image data has been received from the radiation detector 36. At step S27, the CPU 50A stores the acquired image data in the external storage device 50D.

At step S28, the CPU 50A notifies the FPD controller 350 of the radiation detector 36 that image data for the radiation image of 2D imaging has been received correctly. On receipt of the notification from the CPU 50A that the image data has been received correctly, the FPD controller 350 of the radiation detector 36 transitions to the reset mode to remove accumulated charges from the respective capacitors 210 of the pixels 220.

At step S29, the CPU 50A transmits a control signal to the erasing light source driver 39 to start activation of the erasing light. The erasing light source driver 39 that has received the control signal from the CPU 50A supplies a drive signal to the erasing light source 38, placing the erasing light source 38 in the activated state. The radiation detector 36 is accordingly illuminated with erasing light, promoting disappearance of residual charge remaining in the sensor portions 100 of the radiation detector 36, and erasing the lag image.

At step S30, the CPU 50A determines whether or not a specific duration (for example 5 seconds) has elapsed since transition of the erasing light source 38 to the activated state. Processing transitions to step S31 if the CPU 50A determines that the specific duration has elapsed. The specific duration may be set as appropriate to a sufficient duration for charge remaining in the sensor portions 100 of the radiation detector 36 to disappear.

At step S31, the CPU 50A transmits a control signal to the erasing light source driver 39 to deactivate the erasing light. The erasing light source driver 39 that has received the control signal from the CPU 50A places the erasing light source 38 in the deactivated state. The routine of the respective steps described above then ends.

As made clear in the above explanation, in the radiation image capture device 10 according to the present exemplary embodiment, the erasing light source 38 is activated continuously during acquisition of plural radiation images when performing tomosynthesis imaging, in which plural radiation images are acquired by successively irradiating radiation over a comparatively short irradiation duration while varying the irradiation angle. Offset variation in the radiation detector 36 can accordingly be prevented due to maintaining activation of the erasing light throughout a period from the start to the end of tomosynthesis imaging, without switching between activation and deactivation of the erasing light corresponding to imaging timings of the plural radiation images. Maintaining activation of the erasing light throughout the period of tomosynthesis imaging moreover enables the disappearance of residual charge remaining in the sensor portions 100 of the radiation detector 36 to be achieved at each radiation image capture, enabling the occurrence of lag images to be suppressed. In the tomosynthesis imaging, the irradiation duration of one shot of radiation is comparatively short, at approximately 100 msec, so pronounced non-uniformities in radiation images do not occur even when the erasing light is activated during radiation image capture (when in the accumulation mode and when in the read mode), and thus present substantially no issue.

When performing 2D imaging in the radiation image capture device 10, the erasing light source 38 is deactivated during radiation image acquisition, in which a radiation image is acquired by irradiating radiation at the specific angle for a longer duration than the irradiation duration in tomosynthesis imaging. The occurrence of non-uniformities in the acquired radiation image can accordingly be prevented. The erasing light source 38 is placed in the activated state after 2D imaging has ended (after charge reading). The disappearance of residual charge remaining in the sensor portions 100 of the radiation detector 36 is thereby achieved, erasing a lag image.

In the radiation image capture device 10 according to the first exemplary embodiment of the present invention, radiation images with better image quality than hitherto can be obtained in both the tomosynthesis imaging mode in which the radiation irradiation duration is comparatively short and radiation images are successively captured, and in the 2D imaging mode in which the radiation irradiation duration is comparatively long.

Second Exemplary Embodiment

Explanation follows regarding a second exemplary embodiment of the present invention. In the first exemplary embodiment, explanation has been given regarding an imaging sequence in which a series of radiation images are acquired by tomosynthesis imaging, in which radiation is successively irradiated at different irradiation angles to acquire plural radiation images, followed by 2D imaging, in which radiation is irradiated at a specific irradiation angle to acquire a radiation image after the tomosynthesis imaging. In contrast, a radiation image capture device 10 according to the second exemplary embodiment acquires a series of radiation images by an imaging sequence in which 2D imaging is performed, and then tomosynthesis imaging is performed after the 2D imaging.

Figure 10:
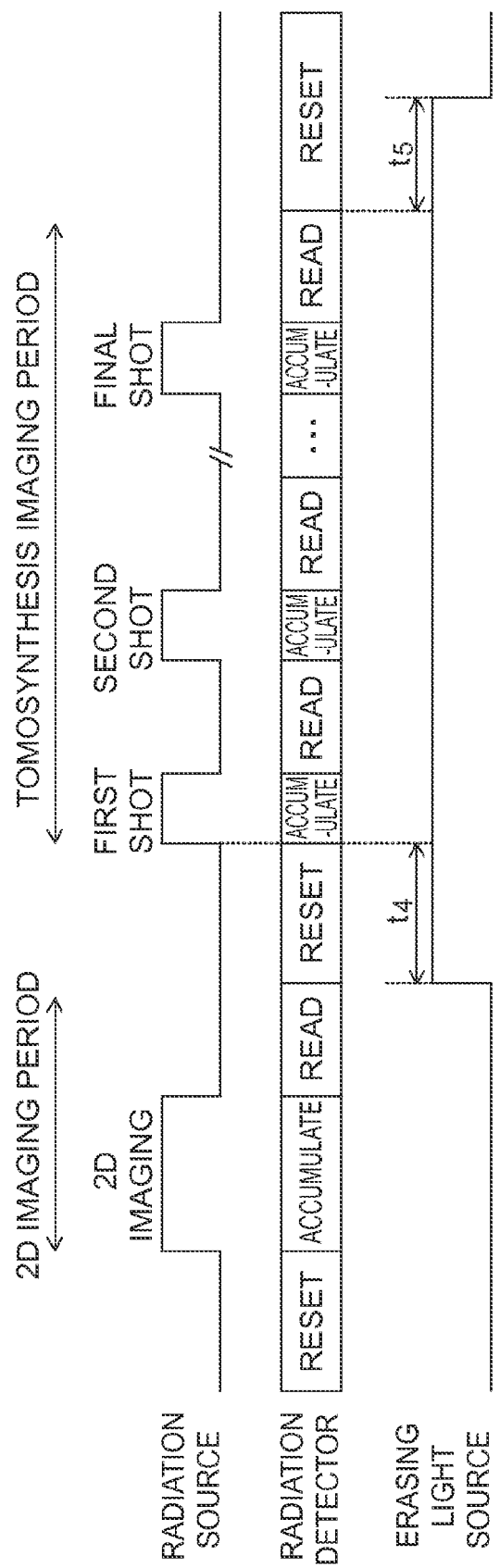
FIG. 10 is a timing chart illustrating operation timings of respective sections of a radiation image capture device according to an exemplary embodiment of the present invention.

FIG. 10 is a timing chart illustrating operation timings of respective sections of the radiation image capture device 10 in a case in which 2D imaging is followed by tomosynthesis imaging.

In a period prior to starting radiation irradiation for 2D imaging, the radiation detector 36 enters the reset mode to reset each of the pixels 220. The radiation detector 36 stops the reset mode prior to starting radiation irradiation for 2D imaging. Moreover, the erasing light source 38 is placed in the deactivated state from a step prior to starting radiation irradiation for 2D imaging.

2D imaging starts once reset has been completed for each of the pixels 220 in the radiation detector 36. The radiation detector 36 transitions to the accumulation mode at a timing for performing radiation irradiation for 2D imaging. Moreover, in the present exemplary embodiment, the irradiation duration (charge accumulation duration in the radiation detector 36) for an exposure in 2D imaging is approximately 1 to 6 seconds. The erasing light source 38 maintains the deactivated state throughout the accumulation period.

The radiation detector 36 transitions to the read mode at a timing of the end of radiation irradiation for 2D imaging. The read charges are supplied to the signal processor 340, and image data is generated for a radiation image by 2D imaging. The erasing light source 38 maintains the deactivated state throughout the charge reading period in 2D imaging.

The radiation detector 36 transitions to the reset mode on completion of charge reading, and the TFTs 202 connected to each of the gate lines 310 are placed in the ON state in sequence to discharge the accumulated charges in the capacitors 210. The erasing light source 38 transitions to the activated state at a timing of charge reading completion. Placing the erasing light source 38 in the activated state erases a lag image due to the 2D imaging. In order to reliably erase the lag image due to the 2D imaging and also to prevent the occurrence of offset variation in the tomosynthesis imaging performed subsequently to the 2D imaging, the erasing light source 38 is preferably activated for as long a duration as possible prior to transitioning to tomosynthesis imaging. In the present exemplary embodiment, a duration of 1 second or longer is secured for a period $t_4$ from the start of erasing light source 38 activation until the start of the initial radiation irradiation (first shot) of tomosynthesis imaging. In the present exemplary embodiment, the period $t_4$ is maximized since the erasing light source 38 transitions to the activated state at the point of charge reading completion in 2D imaging. Note that the erasing light source 38 may transition to the activated state during the reset period after the end of 2D imaging.

Processing transitions to tomosynthesis imaging when reset has been completed for each of the pixels 220 in the radiation detector 36. The radiation detector 36 transitions to the accumulation mode at a timing when the initial radiation irradiation (first shot) of tomosynthesis imaging is performed. Note that in the present exemplary embodiment, the irradiation duration for a single time of radiation during tomosynthesis imaging is approximately 100 msec.

The radiation detector 36 transitions to the read mode at a timing of completion of the first shot. The read charges are supplied to the signal processor 340, and image data is generated for a radiation image corresponding to the irradiation angle.

When charge reading has been completed following the first shot, radiation irradiation is performed for a second time (a second shot) at a different irradiation angle to the first shot. Similarly to the first shot, the radiation detector 36 transitions to the accumulation mode at a timing of radiation irradiation start, and transitions to the read mode at a timing of radiation irradiation end. Radiation irradiation is subsequently performed plural times while varying the radiation irradiation angle in sequence, with the radiation detector 36 repeating charge accumulation and reading in coordination with the radiation irradiation timings.

The radiation detector 36 transitions to the reset mode on completion of charge reading following the final shot. Moreover, the erasing light source 38 transitions to the deactivated state at a timing when a period $t_5$ has elapsed after the completion of charge reading for the final shot. In the present exemplary embodiment, the period $t_5$ is set at approximately 5 seconds, securing a sufficient period for the lag image from tomosynthesis imaging to be erased.

Similarly to in the first exemplary embodiment, in the radiation image capture device 10 according to the present exemplary embodiment, the erasing light source 38 maintains the activated state during acquisition of plural radiation images while switching the radiation irradiation angle in tomosynthesis imaging. Lag images arising at each radiation image capture can accordingly be erased. In tomosynthesis imaging, image non-uniformities are not liable to occur even when imaging is performed in an illuminated state of the erasing light, since the irradiation duration of one shot is approximately 100 msec, this being much shorter than that during 2D imaging (approximately 1 to 6 seconds).

Offset variation in the radiation detector 36 can be prevented since the erasing light is not switched on and off in coordination with the radiation irradiation timings over plural shots.

Moreover, charges in the sensor portions 100 of the radiation detector 36 can attain a stable state by the point when tomosynthesis imaging starts since the erasing light source 38 transitions to the activated state prior to the start of tomosynthesis imaging. A certain amount of time is required for charges in the photoconductor layer 103 to attain a stable state after transition of the erasing light source 38 to the activated state or the deactivated state. In the present exemplary embodiment, a duration of 1 second or longer is secured for the period $t_4$ from transition of the erasing light source 38 to the activated state until the first shot is performed in tomosynthesis imaging, thereby enabling charges in the sensor portions 100 of the radiation detector 36 to attain a stable state by the time of transition to the accumulation mode. Offset variation can accordingly be even more effectively prevented. Note that, within a range for which a tolerable amount of offset variation, the period $t_4$ may be set to a shorter duration or a longer duration than 1 second, and may be varied as appropriate in consideration of the transition period from the 2D imaging mode to the tomosynthesis imaging mode, for example. Transition of the erasing light source 38 to the activated state at the point of charge reading completion in 2D imaging, as in the present exemplary embodiment, enables the period $t_4$ to be maximized.

A lag image can be reliably erased due to securing a duration of approximately 5 seconds for the period $t_5$ until the erasing light source 38 transitions to the deactivated state after completion of charge reading following the final shot in tomosynthesis imaging. Note that it is sufficient to secure an adequate duration to erase the lag image for the period $t_5$, and a shorter duration or a longer duration than 5 seconds may be set.

In 2D imaging, the radiation irradiation duration is comparatively long, at approximately 1 to 6 seconds, and there is a concern of image non-uniformities arising if the radiation detector 36 is illuminated with erasing light during the imaging period. In the radiation image capture device 10 according to the present exemplary embodiment, the erasing light source 38 maintains the deactivated state throughout radiation irradiation for 2D imaging, and the accumulation and reading of charges in the radiation detector 36, enabling non-uniformities to be prevented from occurring in the acquired radiation image.

Figure 11:
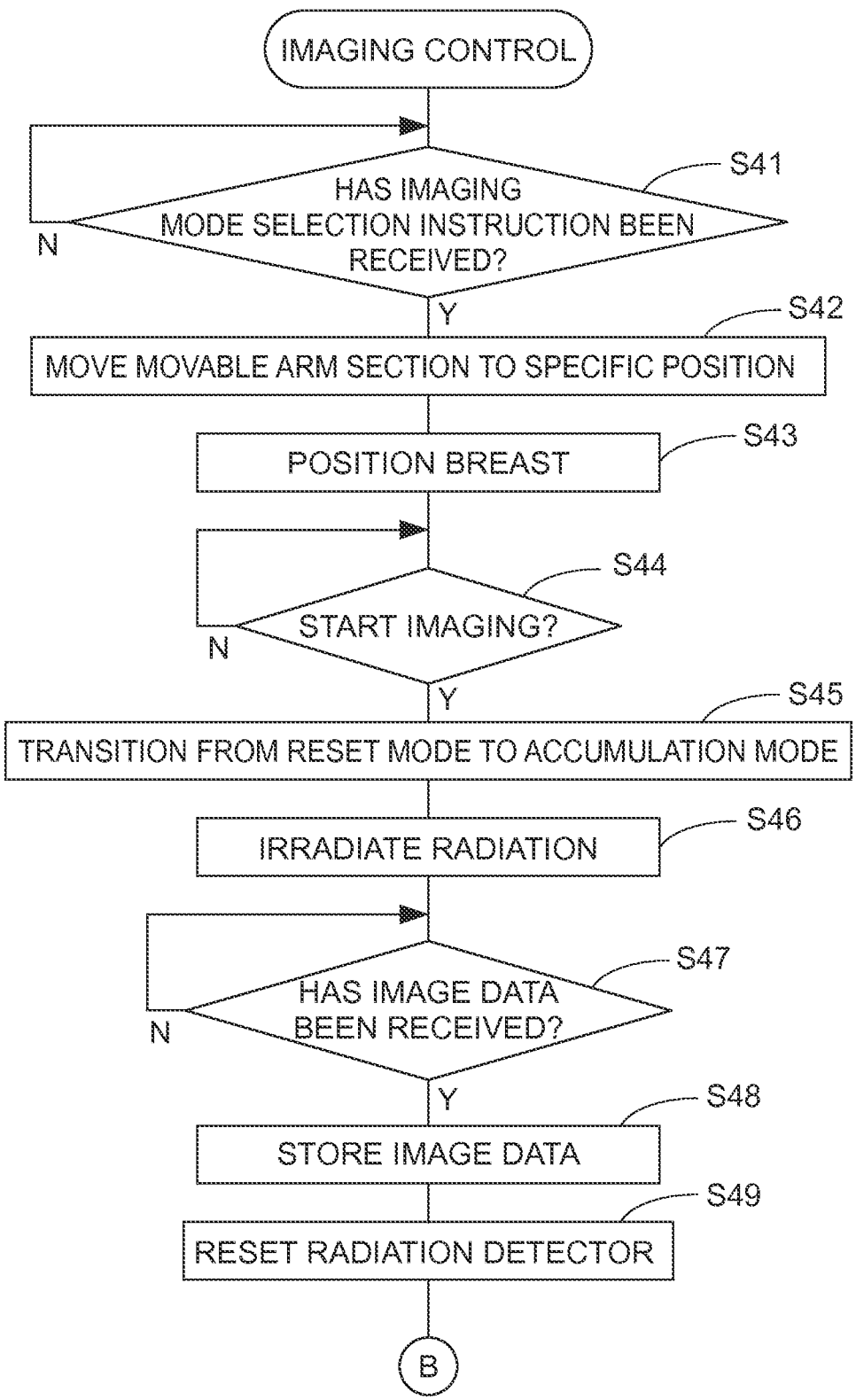
FIG. 11 is a flowchart illustrating a processing flow in an imaging control program according to an exemplary embodiment of the present invention.
Figure 12:
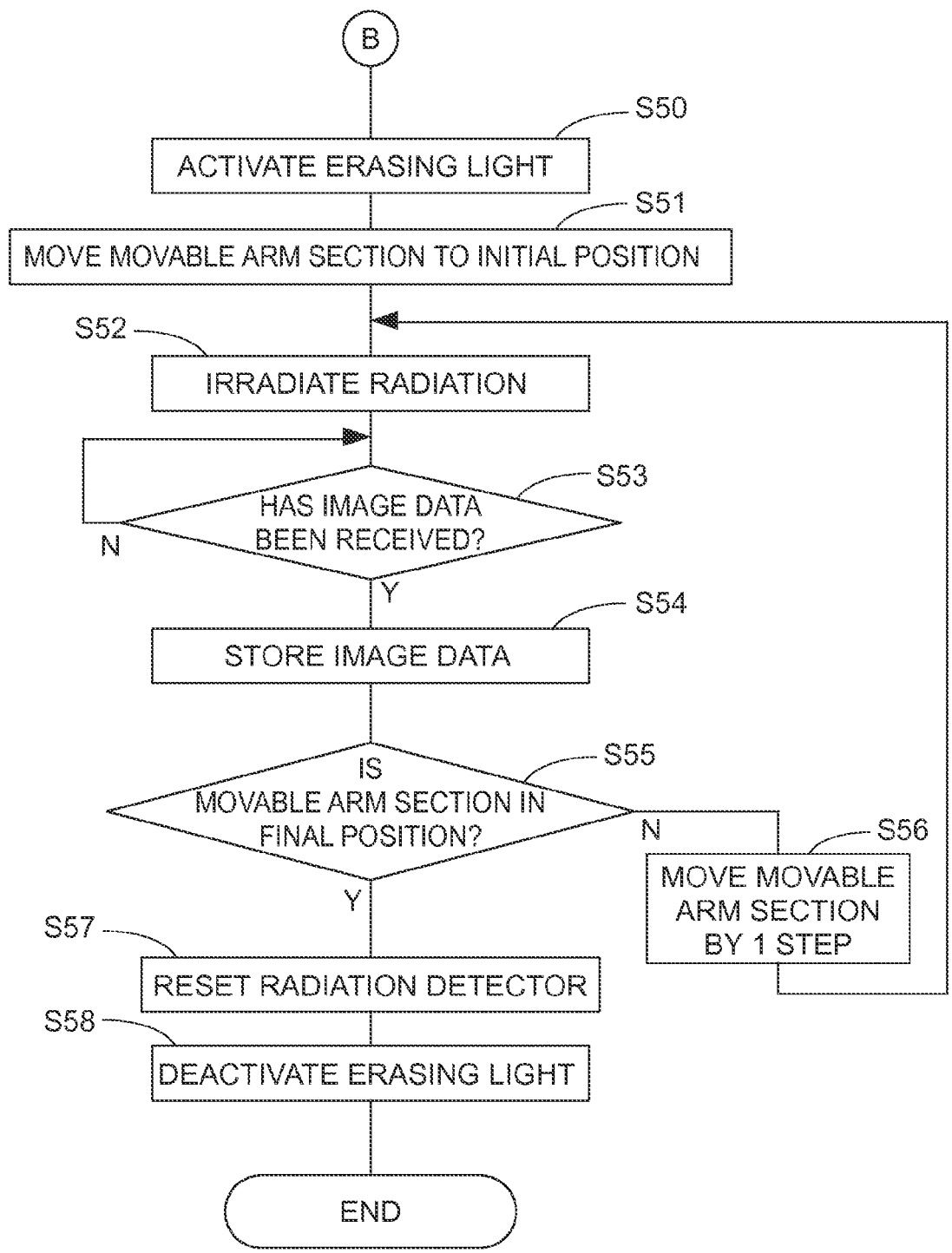
FIG. 12 is a flowchart illustrating a processing flow in an imaging control program according to an exemplary embodiment of the present invention.

FIG. 11 and FIG. 12 are flowcharts illustrating a processing flow of an imaging control program according to the second exemplary embodiment executed by the CPU 50A configuring the main controller 50. The imaging control program is stored in the ROM 50B. The flowcharts in FIG. 11 and FIG. 12 correspond to the timing chart illustrated in FIG. 10. Note that the erasing light source 38 is in the deactivated state at the point when execution of the imaging control program starts.

At step S41, the CPU 50A performs reception standby for an imaging mode selection instruction. A user is able to perform imaging mode selection by operating the operation panel 48. Note that here, an imaging mode is selected in which 2D imaging, in which radiation is irradiated from a single direction to acquire a radiation image, is followed by tomosynthesis imaging, in which radiation is irradiated from plural directions to acquire plural radiation images. Processing transitions to step S42 when the CPU 50A has received an imaging mode selection instruction from the operation panel 48.

At step S42, the CPU 50A transmits a control signal to the movable part drive mechanism 60 to move the rotation angle position of the movable arm section 16 to a specific position for performing 2D imaging. The movable part drive mechanism 60 that has received the control signal from the CPU 50A, for example, moves the movable arm section 16 such that the radiation irradiation direction is orthogonal to the detection face of the radiation detector 36 (namely such that the irradiation angle is 0°). Note that the radiation irradiation direction in 2D imaging may be the same as the irradiation direction at the first shot of tomosynthesis imaging.

At step S43, the breast M is positioned with respect to the imaging table.

At step S44, the CPU 50A determines whether or not 2D imaging start has been instructed. Processing transitions to step S45 when the user has, for example, operated an imaging button (not illustrated in the drawings) to instruct 2D imaging start.

At step 45, the CPU 50A notifies the FPD controller 350 of the radiation detector 36 that radiation irradiation preparation has been completed. On receipt of notification that radiation irradiation preparation has been completed, the FPD controller 350 of the radiation detector 36 transitions from the reset mode, in which accumulated charges are removed from the respective capacitors 210 of the pixels 220, to the accumulation mode.

At step S46, the CPU 50A transmits a control signal to the radiation source driver 27 to start radiation irradiation for 2D imaging. The radiation source driver 27 that has received the control signal from the CPU 50A drives the radiation source 26 to perform radiation irradiation under specific irradiation conditions. Radiation is accordingly irradiated from the radiation source 26 toward the breast M. Note that the radiation irradiation duration at step S46 is approximately 1 second. The radiation irradiates the radiation detector 36 through the breast M. The radiation detector 36 transitions to the accumulation mode and the read mode in coordination with the radiation irradiation timing, generating image data for a radiation image corresponding to the radiation intensity distribution of the irradiated radiation that has passed through the breast M. The generated image data is transmitted to the CPU 50A.

At step S47, the CPU 50A performs standby for image data receipt from the radiation detector 36, and processing transitions to step S48 when the image data has been received from the radiation detector 36. At step S48, the CPU 50A stores the acquired image data in the external storage device 50D.

At step S49, the CPU 50A notifies the FPD controller 350 of the radiation detector 36 that image data for the radiation image of 2D imaging has been received correctly. On receipt of the notification that the image data has been received correctly by the CPU 50A, the FPD controller 350 of the radiation detector 36 transitions to the reset mode to remove accumulated charges from the respective capacitors 210 of the pixels 220. 2D imaging is completed by the respective processing described above, and transition is made to tomosynthesis imaging.

At step S50, the CPU 50A transmits a control signal to the erasing light source driver 39 to start activation of the erasing light. The erasing light source driver 39 that has received the control signal from the CPU 50A supplies a drive signal to the erasing light source 38, placing the erasing light source 38 in the activated state. The radiation detector 36 is accordingly illuminated with erasing light, promoting disappearance of residual charge remaining in the sensor portions 100 of the radiation detector 36, and erasing the lag image.

At step S51, the CPU 50A transmits a control signal to the movable part drive mechanism 60 to move the rotation angle position of the movable arm section 16 to the initial position. The movable part drive mechanism 60 that has received the control signal from the CPU 50A moves the movable arm section 16 to a rotation angle position of maximum tilt (the −X° position in FIG. 3), for example. Note that in cases in which the angle position of the movable arm section 16 in 2D imaging is the same as the angle position at the first shot in tomosynthesis imaging, the processing of step S51 may be omitted. When imaging preparation has been completed, the radiation detector 36 transitions from the reset mode to the accumulation mode.

At step S52, the CPU 50A transmits a control signal to the radiation source driver 27 to start radiation irradiation for tomosynthesis imaging. The radiation source driver 27 that has received the control signal from the CPU 50A drives the radiation source 26 to perform radiation irradiation under specific irradiation conditions. Radiation is accordingly irradiated from the radiation source 26 toward the breast M. Note that the radiation irradiation duration at step S52 is approximately 100 msec. The radiation irradiates the radiation detector 36 through the breast M. The radiation detector 36 transitions to the accumulation mode and the read mode in coordination with the radiation irradiation timing, generating image data for a radiation image corresponding to the radiation intensity distribution of the irradiated radiation that has passed through the breast M. The generated image data is transmitted to the CPU 50A.

At step S53, the CPU 50A performs standby for image data receipt from the radiation detector 36, and when the image data has been received from the radiation detector 36, processing transitions to step S54. At step S54, the CPU 50A stores the acquired image data in the external storage device 50D.

At step S55, the CPU 50A determines whether or not the rotation angle position of the movable arm section 16 is at the final position (the +X° position in the present exemplary embodiment). Processing transitions to step S56 if the CPU 50A determines that the movable arm section 16 is not at the final position, and processing transitions to step S57 if the CPU 50A determines that the movable arm section 16 is at the final position.

At step S56, the CPU 50A transmits a control signal to the movable part drive mechanism 60 to move the rotation angle position of the movable arm section 16 by one step in the positive direction. The movable part drive mechanism 60 that has received the control signal from the CPU 50A moves the rotation angle position of the movable arm section 16 by one step in the positive direction. When the movement of the movable arm section 16 is complete, the CPU 50A repeats the processing of step S52 to step S56. Radiation is accordingly irradiated plural times while moving the movable arm section 16 from −X° to +X°, image data is acquired for each angle position of the movable arm section 16, and the acquired image data is respectively stored in the external storage device 50D.

At step S57, the CPU 50A notifies the FPD controller 350 of the radiation detector 36 that all image data for tomosynthesis imaging has been received correctly. On receipt of this notification, the FPD controller 350 of the radiation detector 36 resets each of the pixels 220, removing the accumulated charges in the capacitors 210.

At step S58, the CPU 50A transmits a control signal to the erasing light source driver 39 to deactivate the erasing light. The erasing light source driver 39 that has received the control signal from the CPU 50A places the erasing light source 38 in the deactivated state. The routine of the respective processes described above then ends.

According to the radiation image capture device 10 of the second exemplary embodiment of the present invention, similarly to in the first exemplary embodiment, the erasing light source 38 is activated continuously during acquisition of plural radiation images in the tomosynthesis imaging mode, in which the radiation irradiation duration is comparatively short and plural radiation images are successively captured, and the erasing light source 38 is deactivated during acquisition of a radiation image in the 2D imaging mode with a comparatively long radiation irradiation duration. Radiation images with better image quality than hitherto can accordingly be obtained in both the tomosynthesis imaging mode and the 2D imaging mode.

Third Exemplary Embodiment

Explanation follows regarding a third exemplary embodiment of the present invention. In the first and second exemplary embodiments, examples are given in which tomosynthesis imaging and 2D imaging are performed successively. In contrast, a radiation image capture device 10 according to the third exemplary embodiment performs tomosynthesis imaging and 2D imaging independently of one another.

FIG. 13A is a timing chart illustrating operation timings of respective sections of the radiation image capture device 10 in a case in which 2D imaging is performed on its own. FIG. 13B is a timing chart illustrating operation timings of respective sections of the radiation image capture device 10 in a case in which tomosynthesis imaging is performed on its own.

In a period prior to starting radiation irradiation for 2D imaging, the radiation detector 36 enters the reset mode to reset each of the pixels 220. The radiation detector 36 stops the reset mode prior to starting radiation irradiation for 2D imaging. Moreover, the erasing light source 38 is placed in the deactivated state from a step prior to starting radiation irradiation for 2D imaging.

2D imaging starts once reset has been completed for each of the pixels 220 in the radiation detector 36. The radiation detector 36 transitions to the accumulation mode at a timing for performing radiation irradiation for 2D imaging. Moreover, in the present exemplary embodiment, the irradiation duration (charge accumulation duration in the radiation detector 36) for an exposure in 2D imaging is approximately 1 to 6 seconds. The erasing light source 38 maintains the deactivated state throughout the accumulation period.

The radiation detector 36 transitions to the read mode at a timing of the end of radiation irradiation for 2D imaging. The read charges are supplied to the signal processor 340, and image data is generated for a radiation image by 2D imaging. The erasing light source 38 maintains the deactivated state throughout the charge reading period in 2D imaging.

The radiation detector 36 transitions to the reset mode on completion of charge reading, and the TFTs 202 connected to each of the gate lines 310 are switched ON in sequence to discharge the accumulated charges in the capacitors 210. The erasing light source 38 transitions to the activated state at a timing of charge reading completion. In the present exemplary embodiment, an activation period $t_6$ of the erasing light source 38 is set at 5 seconds, thereby securing a sufficient duration to erase the lag image due to 2D imaging.

Explanation follows regarding a case in which tomosynthesis imaging is performed on its own, with reference to FIG. 13B.

The radiation detector 36 resets each of the pixels 220 and stops the reset mode prior to the start of the initial radiation irradiation (first shot) of tomosynthesis imaging.

Moreover, the erasing light source 38 transitions to the activated state at a timing prior to the start of the initial radiation irradiation (first shot). In the present exemplary embodiment, a duration of 1 second or longer is secured for a period $t_7$ from the start of erasing light source 38 activation until the first shot is started. The erasing light source 38 maintains the activated state throughout the period of tomosynthesis imaging.

The radiation detector 36 transitions to the accumulation mode at a timing when the first shot is performed. Note that in the present exemplary embodiment, the irradiation duration (charge accumulation duration in the radiation detector 36) for one shot in tomosynthesis imaging is approximately 100 msec.

The radiation detector 36 transitions to the read mode at a timing of completion of the first shot, and image data is generated for a radiation image corresponding to the irradiation angle.

When charge reading has been completed following the first shot, radiation irradiation is performed for a second time (a second shot) at a different irradiation angle to the first shot. Similarly to in the first shot, the radiation detector 36 transitions to the accumulation mode at a timing of radiation irradiation start, and transitions to the read mode at a timing of radiation irradiation end. Radiation irradiation is subsequently performed plural times while varying the radiation irradiation angle in sequence, the radiation detector 36 repeating charge accumulation and reading in coordination with the radiation irradiation timings.

The radiation detector 36 transitions to the reset mode on completion of charge reading following the final shot. Moreover, the erasing light source 38 transitions to the deactivated state at a timing when a period $t_8$ has elapsed after the completion of charge reading for the final shot. In the present exemplary embodiment, the period $t_8$ is set at approximately 5 seconds, securing a sufficient period for the lag image from tomosynthesis imaging to be erased.

Similarly to in the first and second exemplary embodiments, in the radiation image capture device 10 according to the present exemplary embodiment, the erasing light source 38 maintains the activated state during acquisition of plural radiation images while switching the radiation irradiation angle in tomosynthesis imaging. Lag images arising at each radiation image capture can accordingly be erased. In tomosynthesis imaging, image non-uniformities are not liable to occur even when imaging is performed in an illuminated state of the erasing light, since the irradiation duration of one shot is approximately 100 msec, this being much shorter than that during 2D imaging (approximately 1 to 6 seconds).

Offset variation in the radiation detector 36 can be prevented since the erasing light is not switched on and off in coordination with the radiation irradiation timings over plural shots.

Moreover, charges in the sensor portions 100 of the radiation detector 36 can attain a stable state by the point when tomosynthesis imaging starts since the erasing light source 38 transitions to the activated state prior to the start of tomosynthesis imaging. In the present exemplary embodiment, a duration of 1 second or longer is secured for the period $t_7$ from transition of the erasing light source 38 to the activated state until the first shot is performed, thereby enabling charges in the sensor portions 100 of the radiation detector 36 to attain a stable state by the time of transition to the accumulation mode. Offset variation can accordingly be even more effectively prevented. Note that, within a range for which a tolerable amount of offset variation, the period $t_7$ may be set to a shorter period or a longer period than 1 second.

A lag image can be reliably erased due to securing a duration of approximately 5 seconds for the period $t_8$ until the erasing light source 38 transitions to the deactivated state after completion of charge reading following the final shot in tomosynthesis imaging. Note that it is sufficient to secure an adequate duration to erase the lag image for the period $t_8$, and a shorter duration or a longer duration than 5 seconds may be set.

In 2D imaging, the radiation irradiation duration is comparatively long, at approximately 1 to 6 seconds, and there is a concern of image non-uniformities arising if the radiation detector 36 is illuminated with erasing light during the imaging period. In the radiation image capture device 10 according to the present exemplary embodiment, the erasing light source 38 maintains the deactivated state throughout radiation irradiation for 2D imaging, and the accumulation and reading of charges in the radiation detector 36, enabling the occurrence of non-uniformities to be prevented.

FIG. 14 is a flowchart illustrating a processing flow in an imaging control program according to the third exemplary embodiment executed in a case in which the CPU 50A configuring the main controller 50 performs 2D imaging on its own, and corresponds to the timing chart illustrated in FIG. 13A. The imaging control program is stored in the ROM 50B. Note that the erasing light source 38 is in the deactivated state at the point when execution of the imaging control program starts.

At step S61, the CPU 50A performs reception standby for an imaging mode selection instruction. A user is able to perform imaging mode selection by operating the operation panel 48. Note that here, an imaging mode is selected in which 2D imaging, in which radiation is irradiated from a single direction to acquire a radiation image, is performed on its own. Processing transitions to step S62 when the CPU 50A has received an imaging mode selection instruction from the operation panel 48.

At step S62, the CPU 50A transmits a control signal to the movable part drive mechanism 60 to move the rotation angle position of the movable arm section 16 to a specific position for performing 2D imaging. The movable part drive mechanism 60 that has received the control signal from the CPU 50A, for example, moves the movable arm section 16 such that the radiation irradiation direction is orthogonal to the detection face of the radiation detector 36 (namely such that the irradiation angle is 0°).

At step S63, the breast M is positioned with respect to the imaging table.

At step S64, the CPU 50A determines whether or not 2D imaging start has been instructed. Processing transitions to step S65 when the user has, for example, operated an imaging button (not illustrated in the drawings) to instruct 2D imaging start.

At step S65, the CPU 50A notifies the FPD controller 350 of the radiation detector 36 that radiation irradiation preparation has been completed. On receipt of notification from the CPU 50A that radiation irradiation preparation has been completed, the FPD controller 350 of the radiation detector 36 transitions from the reset mode, in which accumulated charges are removed from the respective capacitors 210 of the pixels 220, to the accumulation mode.

At step S66, the CPU 50A transmits a control signal to the radiation source driver 27 to start radiation irradiation for 2D imaging. The radiation source driver 27 that has received the control signal from the CPU 50A drives the radiation source 26 to perform radiation irradiation under specific irradiation conditions. Radiation is accordingly irradiated from the radiation source 26 toward the breast M. Note that the radiation irradiation duration at step S66 is approximately 1 second. The radiation irradiates the radiation detector 36 through the breast M. The radiation detector 36 transitions to the accumulation mode and the read mode in coordination with the radiation irradiation timing, generating a radiation image corresponding to the radiation intensity distribution of the irradiated radiation that has passed through the breast M. Image data expressing the radiation image is transmitted to the CPU 50A.

At step S67, the CPU 50A performs standby for image data receipt from the radiation detector 36, and when the image data has been received from the radiation detector 36, processing transitions to step S68. At step S68, the CPU 50A stores the acquired image data in the external storage device 50D.

At step S69, the CPU 50A notifies the FPD controller 350 of the radiation detector 36 that image data for 2D imaging has been received correctly. On receipt of the notification that the image data has been received correctly by the CPU 50A, the FPD controller 350 of the radiation detector 36 transitions to the reset mode to remove accumulated charges from the respective capacitors 210 of the pixels 220.

At step S70, the CPU 50A transmits a control signal to the erasing light source driver 39 to start activation of the erasing light. The erasing light source driver 39 that has received the control signal from the CPU 50A supplies a drive signal to the erasing light source 38, placing the erasing light source 38 in the activated state. The radiation detector 36 is accordingly illuminated with erasing light, promoting disappearance of residual charge remaining in the sensor portions 100 of the radiation detector 36, and erasing the lag image.

At step S71, the CPU 50A determines whether or not a specific duration (for example 5 seconds) has elapsed since transition of the erasing light source 38 to the activated state. Processing transitions to step S72 if the CPU 50A determines that the specific duration has elapsed. The specific duration may be set as appropriate to a sufficient duration for charge remaining in the sensor portions 100 of the radiation detector 36 to disappear.

At step S72, the CPU 50A transmits a control signal to the erasing light source driver 39 to deactivate the erasing light. The erasing light source driver 39 that has received the control signal from the CPU 50A places the erasing light source 38 in the deactivated state. The routine of the respective processes described above then ends.

FIG. 15 is a flowchart illustrating a processing flow in an imaging control program according to the third exemplary embodiment executed in a case in which the CPU 50A configuring the main controller 50 performs tomosynthesis imaging on its own, and corresponds to the timing chart illustrated in FIG. 13B. The imaging control program is stored in the ROM 50B. Note that the erasing light source 38 is in the deactivated state at the point when execution of the imaging control program starts.

At step S81, the CPU 50A performs reception standby for an imaging mode selection instruction. A user is able to perform imaging mode selection by operating the operation panel 48. Note that here, an imaging mode is selected in which tomosynthesis imaging, in which radiation is successively irradiated from plural directions to acquire plural radiation images, is performed on its own. Processing transitions to step S82 when the CPU 50A has received an imaging mode selection instruction from the operation panel 48.

At step S82, the breast M is positioned with respect to the imaging table.

At step S83, the CPU 50A determines whether or not tomosynthesis imaging start has been instructed. Processing transitions to step S84 when the user has, for example, operated an imaging button (not illustrated in the drawings) to instruct tomosynthesis imaging start.

At step S84, the CPU 50A transmits a control signal to the movable part drive mechanism 60 to move a rotation angle position of the movable arm section 16 to an initial position. The movable part drive mechanism 60 that has received the control signal from the CPU 50A moves the movable arm section 16 to a rotation angle position of maximum tilt (the −X° position in FIG. 3), for example.

At step S85, the CPU 50A transmits a control signal to the erasing light source driver 39 to start activation of the erasing light. The erasing light source driver 39 that has received the control signal from the CPU 50A supplies a drive signal to the erasing light source 38, placing the erasing light source 38 in the activated state. The radiation detector 36 is accordingly illuminated with erasing light.

At step S86, the CPU 50A notifies the FPD controller 350 of the radiation detector 36 that radiation irradiation preparation has been completed. On receipt of notification from the CPU 50A that radiation irradiation preparation has been completed, the FPD controller 350 of the radiation detector 36 transitions from the reset mode, in which accumulated charges are removed from the respective capacitors 210 of the pixels 220, to the accumulation mode.

At step S87, the CPU 50A transmits a control signal to the radiation source driver 27 to start radiation irradiation for tomosynthesis imaging. The radiation source driver 27 that has received the control signal from the CPU 50A drives the radiation source 26 to perform radiation irradiation under specific irradiation conditions. Radiation is accordingly irradiated from the radiation source 26 toward the breast M. Note that the radiation irradiation duration at step S87 is approximately 100 msec. The radiation irradiates the radiation detector 36 through the breast M. The radiation detector 36 transitions to the accumulation mode and the read mode in coordination with the radiation irradiation timing, generating a radiation image corresponding to the radiation intensity distribution of the irradiated radiation that has passed through the breast M. Image data expressing the radiation image is transmitted to the CPU 50A.

At step S88, the CPU 50A performs standby for image data receipt from the radiation detector 36, and when the image data has been received from the radiation detector 36, processing transitions to step S89. At step S89, the CPU 50A stores the acquired image data in the external storage device 50D.

At step S90, the CPU 50A determines whether or not the rotation angle position of the movable arm section 16 is at the final position (the +X° position in the present exemplary embodiment). Processing transitions to step S91 if the CPU 50A determines that the movable arm section 16 is not at the final position, and processing transitions to step S92 if the CPU 50A determines that the movable arm section 16 is at the final position.

At step S91, the CPU 50A transmits a control signal to the movable part drive mechanism 60 to move the rotation angle position of the movable arm section 16 by one step in the positive direction. The movable part drive mechanism 60 that has received the control signal from the CPU 50A moves the rotation angle position of the movable arm section 16 by one step in the positive direction. When the movement of the movable arm section 16 is complete, the CPU 50A repeats the processing of step S87 to step S91. Radiation is accordingly irradiated plural times while moving the movable arm section 16 from −X° to +X°, image data is acquired for each angle position of the movable arm section 16, and the acquired image data is respectively stored in the external storage device 50D.

At step S92, the CPU 50A transmits a control signal to the erasing light source driver 39 to deactivate the erasing light. The erasing light source driver 39 that has received the control signal from the CPU 50A places the erasing light source 38 in the deactivated state. The routine of the respective processes described above then ends.

According to the radiation image capture device 10 of the third exemplary embodiment of the present invention, similarly to in the first and second exemplary embodiments, the erasing light source 38 is activated continuously during acquisition of plural radiation images in the tomosynthesis imaging mode, in which the radiation irradiation duration is comparatively short and plural radiation images are successively captured, and the erasing light source 38 is deactivated during acquisition of a radiation image in the 2D imaging mode with a comparatively long radiation irradiation duration. Radiation images with better image quality than hitherto can accordingly be obtained in both the tomosynthesis imaging mode and the 2D imaging mode.

Fourth Exemplary Embodiment

In the first to third exemplary embodiments, explanation has been given regarding an example of a tomosynthesis imaging mode as an imaging mode in which plural radiation images are successively acquired by successively irradiating radiation over a shorter irradiation duration than the radiation irradiation duration in 2D imaging. A radiation image capture device 10 according to a fourth exemplary embodiment performs video imaging (fluoroscopy) as an imaging mode in which plural radiation images are successively acquired by successively irradiating radiation over a shorter irradiation duration than the radiation irradiation duration in 2D imaging. Video imaging refers to imaging in which radiation is successively irradiated toward a breast M, this being an imaging subject, from a specific direction and at a specific frame rate to successively generate plural radiation images. The captured images can be displayed in real time on an external monitor connected to the radiation image capture device 10. The frame rate during video imaging is, for example, approximately 10 to 12 frames/second, and the irradiation duration of a single time of irradiation is shorter than that of 2D imaging (still image capture), at approximately several tens of milliseconds.

Figure 16:
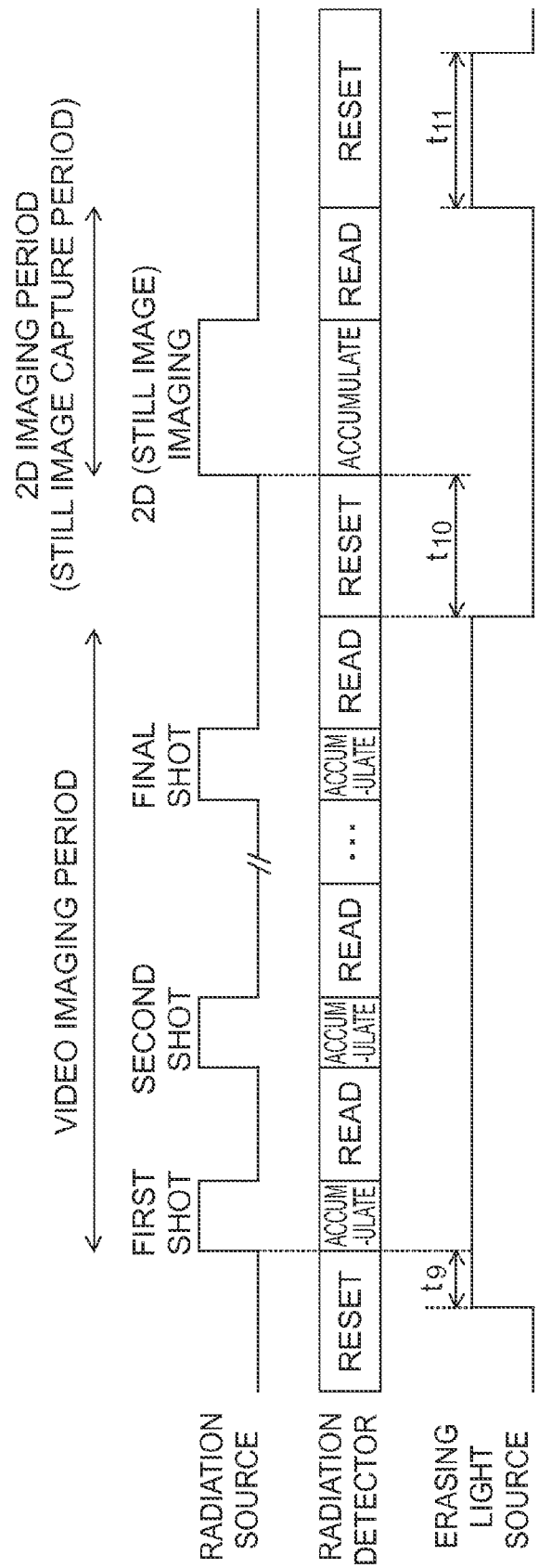
FIG. 16 is a timing chart illustrating operation timings of respective sections of a radiation image capture device according to an exemplary embodiment of the present invention.

FIG. 16 is a timing chart illustrating operation timings of respective sections of the radiation image capture device 10 in a case in which video imaging is followed by 2D imaging (still image capture).

In a period prior to starting radiation irradiation for the initial time (the first shot) in video imaging, the radiation detector 36 resets each of the pixels 220. The radiation detector 36 stops the reset mode prior to the first shot. The erasing light source 38 transitions to the activated state at a timing prior to starting the first shot. In the present exemplary embodiment, a duration of 1 second or longer is secured for a period $t_9$ from the start of erasing light source 38 activation until the first shot is started. The erasing light source 38 maintains the activated state throughout the period of video imaging.

The radiation detector 36 transitions to the accumulation mode at a timing when the first shot is performed. Note that in the present exemplary embodiment, the irradiation duration (charge accumulation duration in the radiation detector 36) for one exposure in video imaging is approximately 50 msec.

The radiation detector 36 transitions to the read mode at a timing of completion of the first shot, and image data is generated for a radiation image corresponding to a first frame.

When charge reading has been completed following the first shot, radiation irradiation is performed for a second time (a second shot). Similarly to the first shot, the radiation detector 36 transitions to the accumulation mode at a timing of radiation irradiation start, and transitions to the read mode and generates image data for a radiation image corresponding to the second frame at a timing of radiation irradiation end. Similar radiation irradiation is subsequently performed plural times, with the radiation detector 36 repeating charge accumulation and reading in coordination with the radiation irradiation timings.

The erasing light source 38 transitions to the deactivated state at a timing of charge reading completion following the final shot when performing radiation irradiation for the last time (the final shot) in video imaging. Namely, the erasing light source 38 maintains the activated state throughout the period from prior to starting the first shot until charge reading has been completed following the final shot. The disappearance of residual charge arising in the sensor portions 100 at each shot is accordingly achieved, erasing lag images at each shot.

The radiation detector 36 transitions to the reset mode when video imaging has been completed. The erasing light source 38 maintains the deactivated state throughout the reset period.

Transition is made to 2D imaging (still image capture) when reset has been completed for each of the pixels 220 in the radiation detector 36. The radiation detector 36 transitions to the accumulation mode at a timing of radiation irradiation for 2D imaging. In the present exemplary embodiment, a duration of 1 second or longer is secured for a period $t_{10}$ from transition of the erasing light source 38 to the deactivated state accompanying the end of video imaging until the start of radiation irradiation for 2D imaging. In the present exemplary embodiment, the irradiation duration (charge accumulation duration in the radiation detector 36) for a single time of radiation in 2D imaging is approximately 1 to 6 seconds. The erasing light source 38 maintains the deactivated state during charge accumulation for 2D imaging by the radiation detector 36.

The radiation detector 36 transitions to the read mode at a timing of the end of radiation irradiation for 2D imaging. Image data is accordingly generated for a radiation image by 2D imaging. The erasing light source 38 maintains the deactivated state during charge accumulation for 2D imaging by the radiation detector 36.

The radiation detector 36 transitions to the reset mode on completion of charge reading. The erasing light source 38 transitions to the activated state at a timing of charge reading completion. The erasing light source 38 maintains the activated state over a period $t_{11}$ that is sufficient for a lag image to be erased (for example 5 seconds), after which the erasing light source 38 transitions to the deactivated state.

In the radiation image capture device 10 according to the present exemplary embodiment, the erasing light source 38 accordingly maintains the activated state during successive acquisition of plural radiation images in the video imaging mode. Lag images arising at each radiation image capture can accordingly be erased. In video imaging, image non-uniformities are not liable to occur even when imaging is performed in an illuminated state of the erasing light, since the irradiation duration of one exposure is approximately several tens of milliseconds, this being much shorter than that during 2D imaging (approximately 1 to 6 seconds).

Offset variation in the radiation detector 36 can be prevented since the erasing light is not switched on and off in coordination with the radiation irradiation timings over plural shots. Moreover, a duration of 1 second or longer is secured for the period $t_9$ from transition of the erasing light source 38 to the activated state until the first shot is performed, thereby enabling charges in the sensor portions 100 of the radiation detector 36 to attain a stable state by the time of transition to the accumulation mode. Namely, a certain amount of time is required for charges in the photoconductor layer 103 to attain a stable state after transition of the erasing light source 38 to the activated state or the deactivated state. Securing a duration of 1 second or longer for the period $t_9$ accordingly enables charges in the photoconductor layer 103 to attain a stable state by the time of transition to the accumulation mode. Offset variation can accordingly be even more effectively prevented. Note that, within a range for which a tolerable amount of offset variation, the period $t_9$ may be set to a shorter period or a longer period than 1 second.

In 2D imaging, the radiation irradiation duration is comparatively long, at approximately 1 to 6 seconds, and there is a concern of image non-uniformities arising if the radiation detector 36 is illuminated with erasing light during 2D imaging. In the radiation image capture device 10 according to the present exemplary embodiment, the erasing light source 38 maintains the deactivated state throughout radiation irradiation for 2D imaging, and the accumulation and reading of charges in the radiation detector 36, enabling the occurrence of non-uniformities to be prevented.

Moreover, charges in the sensor portions 100 of the radiation detector 36 can attain a stable state by the point when 2D imaging starts, since the erasing light source 38 transitions to the deactivated state prior to the start of 2D imaging. In the present exemplary embodiment, a duration of 1 second or longer is secured for the period $t_{10}$ from transition of the erasing light source 38 to the deactivated state after the end of video imaging until the start of 2D imaging. Charges in the sensor portions 100 of the radiation detector 36 can accordingly attain a stable state at the transition to the accumulation mode during 2D imaging, and offset variation in 2D imaging can be prevented. Note that, within a range for which a tolerable amount of offset variation, the period $t_{10}$ may be may be set to a shorter period or a longer period than 1 second, and may be modified as appropriate in consideration of the transition period from the video imaging mode to the 2D imaging mode, for example. The period $t_{10}$ can be maximized due to the erasing light source 38 transitioning to the deactivated state at the point of charge reading completion following the final shot in video imaging, as in the present exemplary embodiment.

A lag image can be reliably erased due to securing a duration of 5 seconds for the period $t_{11}$ of the activated state of the erasing light source 38 after completion of charge reading in 2D imaging. Note that it is sufficient to secure an adequate duration to erase the lag image for the period $t_{11}$, and a shorter duration or a longer duration than 5 seconds may be set. Moreover, when a sufficient duration to allow residual charge remaining in the sensor portions 100 to disappear naturally is secured after 2D imaging, activation of the erasing light source 38 after 2D imaging may be omitted.

Figure 17:
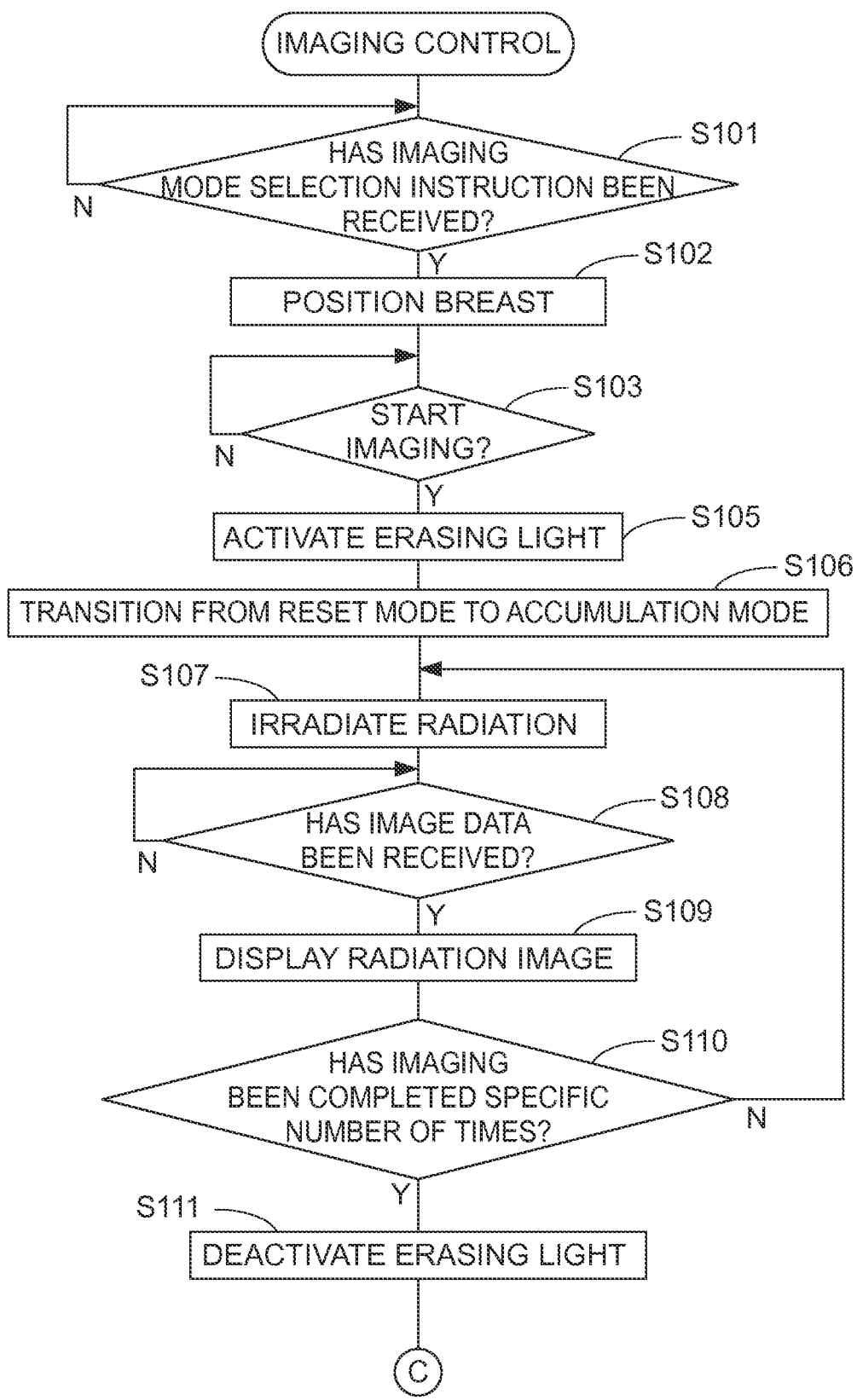
FIG. 17 is a flowchart illustrating a processing flow in an imaging control program according to an exemplary embodiment of the present invention.

FIG. 17 and FIG. 18 are flowcharts illustrating a processing flow of an imaging control program according to the fourth exemplary embodiment executed by the CPU 50A configuring the main controller 50. The imaging control program is stored in the ROM 50B. The flowcharts in FIG. 17 and FIG. 18 correspond to the timing chart illustrated in FIG. 16. Note that the erasing light source 38 is in the deactivated state at the point when execution of the imaging control program starts.

At step S101, the CPU 50A performs reception standby for an imaging mode selection instruction. A user is able to perform imaging mode selection by operating the operation panel 48. Note that here, an imaging mode is selected in which video imaging, in which radiation is successively irradiated at specific time intervals to successively acquire plural radiation images, is followed by 2D imaging (still image capture), in which a single radiation image is acquired. Processing transitions to step S102 when the CPU 50A has received an imaging mode selection instruction from the operation panel 48.

At step S102, the breast M is positioned with respect to the imaging table.

At step S103, the CPU 50A determines whether or not video imaging start has been instructed. Processing transitions to step S105 when the user has, for example, operated an imaging button (not illustrated in the drawings) to instruct video imaging start.

At step 105, the CPU 50A transmits a control signal to the erasing light source driver 39 to start activation of the erasing light. The erasing light source driver 39 that has received the control signal from the CPU 50A supplies a drive signal to the erasing light source 38, placing the erasing light source 38 in the activated state. The radiation detector 36 is accordingly illuminated with erasing light.

At step S106, the CPU 50A notifies the FPD controller 350 of the radiation detector 36 that radiation irradiation preparation has been completed. On receipt of notification from the CPU 50A that radiation irradiation preparation has been completed, the FPD controller 350 of the radiation detector 36 transitions from the reset mode, in which accumulated charges are removed from the respective capacitors 210 of the pixels 220, to the accumulation mode.

At step S107, the CPU 50A transmits a control signal to the radiation source driver 27 to start radiation irradiation for video imaging. The radiation source driver 27 that has received the control signal from the CPU 50A drives the radiation source 26 to perform radiation irradiation under specific irradiation conditions. Radiation is accordingly irradiated from the radiation source 26 toward the breast M. Note that the radiation irradiation duration at step S107 is approximately 50 msec. The radiation irradiates the radiation detector 36 through the breast M. The radiation detector 36 transitions to the accumulation mode and the read mode in coordination with the radiation irradiation timing, generating image data for a radiation image corresponding to the radiation intensity distribution of the irradiated radiation that has passed through the breast M. The generated image data is transmitted to the CPU 50A.

At step S108, the CPU 50A performs standby for image data receipt from the radiation detector 36, and processing transitions to step S109 when the image data has been received from the radiation detector 36. At step S109, the CPU 50A stores the acquired image data in the external storage device 50D, and also outputs the acquired image data to the external monitor. The external monitor displays the radiation image in real time.

At step S110, the CPU 50A determines whether or not capture of a specific number of radiation images has been completed. Processing returns to step S107 if the CPU 50A determines that capture of the specific number of radiation images has not been completed, and processing transitions to step S111 if the CPU 50A determines that capture of the specific number of radiation images has been completed.

The CPU 50A repeats the processing from step S107 to step S110 until capture of the specific number of radiation images has been completed. Video imaging is accordingly performed for a specific number of frames, which are displayed on the external monitor in real time.

At step S111, the CPU 50A transmits a control signal to the erasing light source driver 39 to deactivate the erasing light. The erasing light source driver 39 that has received the control signal from the CPU 50A places the erasing light source 38 in the deactivated state.

At step S112, the CPU 50A determines whether or not 2D imaging start has been instructed. Processing transitions to step S113 when the user has, for example, operated an imaging button (not illustrated in the drawings) to instruct 2D imaging start.

At step S113, the CPU 50A notifies the FPD controller 350 of the radiation detector 36 that radiation irradiation preparation for 2D imaging has been completed. On receipt of notification from the CPU 50A that radiation irradiation preparation has been completed, the FPD controller 350 of the radiation detector 36 transitions from the reset mode, in which accumulated charges are removed from the respective capacitors 210 of the pixels 220, to the accumulation mode.

At step S114, the CPU 50A transmits a control signal to the radiation source driver 27 to start radiation irradiation for 2D imaging. The radiation source driver 27 that has received the control signal from the CPU 50A drives the radiation source 26 to perform radiation irradiation under specific irradiation conditions. Radiation is accordingly irradiated from the radiation source 26 toward the breast M. Note that the radiation irradiation duration at step S114 is approximately 1 to 6 seconds. The radiation irradiates the radiation detector 36 through the breast M. The radiation detector 36 transitions to the accumulation mode and the read mode in coordination with the radiation irradiation timing, generating image data for a radiation image corresponding to the radiation intensity distribution of the irradiated radiation that has passed through the breast M. The generated image data is transmitted to the CPU 50A.

At step S115, the CPU 50A performs standby for image data receipt from the radiation detector 36, and when the image data has been received from the radiation detector 36, processing transitions to step S116. At step S116 the CPU 50A stores the acquired image data in the external storage device 50D.

At step S117, the CPU 50A notifies the FPD controller 350 of the radiation detector 36 that the image data has been received correctly. On receipt of the notification from the CPU 50A that the image data has been received correctly, the FPD controller 350 of the radiation detector 36 transitions to the reset mode to remove accumulated charges from the respective capacitors 210 of the pixels 220.

At step S118, the CPU 50A transmits a control signal to the erasing light source driver 39 to start activation of the erasing light. The erasing light source driver 39 that has received the control signal from the CPU 50A supplies a drive signal to the erasing light source 38, placing the erasing light source 38 in the activated state. The radiation detector 36 is accordingly illuminated with erasing light, promoting disappearance of residual charge remaining in the sensor portions 100 of the radiation detector 36, and erasing the lag image.

At step S119, the CPU 50A determines whether or not a specific duration (for example 5 seconds) has elapsed since transition of the erasing light source 38 to the activated state. Processing transitions to step S120 if the CPU 50A determines that the specific duration has elapsed. The specific duration may be set as appropriate to a sufficient duration for charge remaining in the sensor portions 100 of the radiation detector 36 to disappear.

At step S120, the CPU 50A transmits a control signal to the erasing light source driver 39 to deactivate the erasing light. The erasing light source driver 39 that has received the control signal from the CPU 50A places the erasing light source 38 in the deactivated state. The routine of the respective processes described above then ends.

According to the radiation image capture device of the fourth exemplary embodiment of the present invention, similarly to in the first to third exemplary embodiments, the erasing light source 38 is activated continuously during acquisition of plural radiation images in the video imaging mode, in which the radiation irradiation duration is comparatively short and plural radiation images are successively captured, and the erasing light source 38 is deactivated during acquisition of a radiation image in the 2D imaging (still image capture) mode with a comparatively long radiation irradiation duration. Radiation images with better image quality than hitherto can accordingly be obtained in both the video imaging mode and the 2D imaging mode.

A second aspect of the present invention provides the radiation image capture device of the first aspect, wherein the second imaging mode is a tomosynthesis imaging mode in which the imaging subject is successively irradiated with radiation from the radiation source at plural irradiation angles to successively capture plural radiation images.

A third aspect of the present invention provides the radiation image capture device of the first aspect, wherein the second imaging mode is a video imaging mode in which the imaging subject is successively irradiated with radiation from the radiation source at specific time intervals to successively capture plural radiation images.

A fourth aspect of the present invention provides the radiation image capture device of any one of the first aspect to the third aspect, wherein the first imaging mode is a 2D imaging mode in which the imaging subject is irradiated with radiation from the radiation source at a specific irradiation angle to capture a radiation image.

A fifth aspect of the present invention provides the radiation image capture device of any one of the first aspect to the fourth aspect, wherein the controller places the erasing light source in an activated state after completion of charge reading by the radiation detector in the first imaging mode.

A sixth aspect of the present invention provides the radiation image capture device of any one of the first aspect to the fifth aspect, wherein the controller places the erasing light source in a deactivated state from prior to the start of radiation irradiation in the first imaging mode.

A seventh aspect of the present invention provides the radiation image capture device of any one of the first aspect to the sixth aspect, wherein the controller places the erasing light source in an activated state from prior to the start of initial radiation irradiation in the second imaging mode.

An eighth aspect of the present invention provides the radiation image capture device of any one of the first aspect to the seventh aspect, wherein imaging by the first imaging mode and imaging by the second imaging mode are performed consecutively.

A ninth aspect of the present invention provides the radiation image capture device of the eighth aspect, wherein in cases in which imaging by the first imaging mode is performed after performing imaging by the second imaging mode, the controller places the erasing light source in a deactivated state on completion of charge reading by the radiation detector after final radiation irradiation in the second imaging mode.

A tenth aspect of the present invention provides the radiation image capture device of the eighth aspect, wherein in cases in which imaging by the second imaging mode is performed after performing imaging by the first imaging mode, the controller places the erasing light source in an activated state on completion of charge reading by the radiation detector in the first imaging mode.

An eleventh aspect of the present invention provides the radiation image capture device of any one of the first aspect to the seventh aspect, wherein imaging by the first imaging mode and imaging by the second imaging mode are performed independently of one another.

The present invention is capable of obtaining radiation images with better image quality than hitherto in both an imaging mode in which the radiation irradiation duration is comparatively short and radiation images are successively captured, and in an imaging mode in which the radiation irradiation duration is comparatively long.

What is claimed is:

1. A radiation image capture device comprising:
    a radiation source that irradiates radiation toward an imaging subject;
    a radiation detector that includes a sensor portion configured to generate charges according to radiation irradiated from the radiation source through the imaging subject, that reads charges generated in the sensor portion, and that generates image data of a radiation image;
    an erasing light source that illuminates the radiation detector with erasing light to erase charge remaining in the sensor portion; and
    a controller that, in a first imaging mode in which the radiation detector generates image data of a radiation image based on radiation irradiated from the radiation source over a first irradiation duration, places the erasing light source in a deactivated state at least from a start of radiation irradiation until completion of charge reading by the radiation detector, and that, in a second imaging mode in which the radiation detector generates image data of a plurality of radiation images based on successively irradiated radiation from the radiation source over a second irradiation duration shorter than the first irradiation duration, places the erasing light source in an activated state for at least from a start of initial radiation irradiation until completion of final charge reading by the radiation detector.

2. The radiation image capture device of claim 1, wherein:
    the second imaging mode is a tomosynthesis imaging mode in which the imaging subject is successively irradiated with radiation from the radiation source at a plurality of irradiation angles to successively capture a plurality of radiation images.

3. The radiation image capture device of claim 1, wherein:
    the second imaging mode is a video imaging mode in which the imaging subject is successively irradiated with radiation from the radiation source at specific time intervals to successively capture a plurality of radiation images.

4. The radiation image capture device of claim 1, wherein:
    the first imaging mode is a 2D imaging mode in which the imaging subject is irradiated with radiation from the radiation source at a specific irradiation angle to capture a radiation image.

5. The radiation image capture device of claim 2, wherein:
    the first imaging mode is a 2D imaging mode in which the imaging subject is irradiated with radiation from the radiation source at a specific irradiation angle to capture a radiation image.

6. The radiation image capture device of claim 3, wherein:
the first imaging mode is a 2D imaging mode in which the imaging subject is irradiated with radiation from the radiation source at a specific irradiation angle to capture a radiation image.

7. The radiation image capture device of claim 1, wherein:
the controller places the erasing light source in an activated state after completion of charge reading by the radiation detector in the first imaging mode.

8. The radiation image capture device of claim 2, wherein:
the controller places the erasing light source in an activated state after completion of charge reading by the radiation detector in the first imaging mode.

9. The radiation image capture device of claim 3, wherein:
the controller places the erasing light source in an activated state after completion of charge reading by the radiation detector in the first imaging mode.

10. The radiation image capture device of claim 1, wherein:
the controller places the erasing light source in a deactivated state from prior to the start of radiation irradiation in the first imaging mode.

11. The radiation image capture device of claim 2, wherein:
the controller places the erasing light source in a deactivated state from prior to the start of radiation irradiation in the first imaging mode.

12. The radiation image capture device of claim 3, wherein:
the controller places the erasing light source in a deactivated state from prior to the start of radiation irradiation in the first imaging mode.

13. The radiation image capture device of claim 1, wherein:
the controller places the erasing light source in an activated state from prior to the start of initial radiation irradiation in the second imaging mode.

14. The radiation image capture device of claim 1, wherein:
imaging by the first imaging mode and imaging by the second imaging mode are performed consecutively.

15. The radiation image capture device of claim 14, wherein:
in cases in which imaging by the first imaging mode is performed after performing imaging by the second imaging mode, the controller places the erasing light source in a deactivated state on completion of charge reading by the radiation detector after final radiation irradiation in the second imaging mode.

16. The radiation image capture device of claim 14, wherein:
in cases in which imaging by the second imaging mode is performed after performing imaging by the first imaging mode, the controller places the erasing light source in an activated state on completion of charge reading by the radiation detector in the first imaging mode.

17. The radiation image capture device of claim 1, wherein:
imaging by the first imaging mode and imaging by the second imaging mode are performed independently of one another.

18. A non-transitory computer-readable storage medium stored with a program that causes a computer to function as the controller in the radiation image capture device of claim 1.

19. A control method for an erasing light source in a radiation image capture device comprising a radiation source that irradiates radiation toward an imaging subject, a radiation detector that includes a sensor portion configured to generate charges according to radiation irradiated from the radiation source through the imaging subject, that reads charges generated in the sensor portion, and that generates image data of a radiation image, and an erasing light source that illuminates the radiation detector with erasing light to erase charge remaining in the sensor portion, the control method comprising:
in a first imaging mode in which the radiation detector generates image data of a radiation image based on radiation irradiated from the radiation source over a first irradiation duration, placing the erasing light source in a deactivated state at least from a start of radiation irradiation until completion of charge reading by the radiation detector, and, in a second imaging mode in which the radiation detector generates image data of a plurality of radiation images based on successively irradiated radiation from the radiation source over a second irradiation duration shorter than the first irradiation duration, placing the erasing light source in an activated state for at least from a start of initial radiation irradiation until completion of final charge reading by the radiation detector.

* * * * *